(12) United States Patent
King

(10) Patent No.: US 8,722,079 B2
(45) Date of Patent: May 13, 2014

(54) METHODS FOR TREATING CONDITIONS SUCH AS DYSTONIA AND POST-STROKE SPASTICITY WITH CLONIDINE

(75) Inventor: Vanja Margareta King, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 730 days.

(21) Appl. No.: 12/423,376

(22) Filed: Apr. 14, 2009

(65) Prior Publication Data

US 2009/0263462 A1 Oct. 22, 2009

Related U.S. Application Data

(60) Provisional application No. 61/046,201, filed on Apr. 18, 2008, provisional application No. 61/046,192, filed on Apr. 18, 2008.

(51) Int. Cl.
*A61K 9/00* (2006.01)
*A61P 9/10* (2006.01)

(52) U.S. Cl.
USPC ........................................................ 424/426

(58) Field of Classification Search
USPC ........................................................ 424/426
See application file for complete search history.

(56) References Cited

U.S. PATENT DOCUMENTS

| | | | |
|---|---|---|---|
| 3,190,802 A | 6/1965 | Zeile et al. | |
| 3,020,660 A | 8/1965 | Zeile et al. | |
| 4,624,255 A | 11/1986 | Schenk et al. | |
| 4,742,054 A | 5/1988 | Naftchi | |
| 4,765,974 A | 8/1988 | Tokuda et al. | |
| 4,863,457 A | 9/1989 | Lee | |
| 5,175,052 A | 12/1992 | Tokuda et al. | |
| 5,447,947 A | 9/1995 | Campbell | |
| 5,484,607 A | 1/1996 | Horacek | |
| 5,522,844 A | 6/1996 | Johnson | |
| 5,538,739 A * | 7/1996 | Bodmer et al. | 424/501 |
| 5,626,838 A | 5/1997 | Cavanaugh et al. | |
| 5,635,204 A | 6/1997 | Gervirtz et al. | |
| 5,759,583 A | 6/1998 | Iwamoto | |
| 5,801,188 A | 9/1998 | Hassenbusch, III et al. | |
| 5,868,789 A | 2/1999 | Huebner | |
| 5,869,100 A | 2/1999 | Horacek | |
| 5,942,241 A | 8/1999 | Chasin et al. | |
| 5,942,503 A | 8/1999 | Jung et al. | |
| 5,942,530 A | 8/1999 | Panetta et al. | |
| 5,945,416 A | 8/1999 | Shannon et al. | |
| 5,980,927 A | 11/1999 | Nelson et al. | |
| 6,030,642 A | 2/2000 | Horacek | |
| 6,069,129 A | 5/2000 | Sandberg et al. | |
| 6,147,102 A | 11/2000 | Borgman | |
| 6,153,211 A * | 11/2000 | Hubbell et al. | 424/426 |
| 6,179,862 B1 | 1/2001 | Sawhney | |
| 6,248,345 B1 | 6/2001 | Goldenheim et al. | |
| 6,287,588 B1 | 9/2001 | Shih et al. | |
| 6,326,020 B1 | 12/2001 | Kohane et al. | |
| 6,331,311 B1 | 12/2001 | Broadbeck et al. | |
| 6,417,184 B1 | 7/2002 | Ockert | |
| 6,428,804 B1 | 8/2002 | Suzuki et al. | |
| 6,461,631 B1 | 10/2002 | Dunn et al. | |
| 6,471,688 B1 * | 10/2002 | Harper et al. | 604/892.1 |
| 6,524,607 B1 | 2/2003 | Goldenheim et al. | |
| 6,534,048 B1 | 3/2003 | Borgman | |
| 6,534,081 B2 | 3/2003 | Goldenheim et al. | |
| 6,589,549 B2 | 7/2003 | Shih et al. | |
| 6,630,155 B1 | 10/2003 | Chandrashecar et al. | |
| 6,632,457 B1 | 10/2003 | Sawhney | |
| 6,723,741 B2 | 4/2004 | Jeon et al. | |
| 6,756,058 B2 | 6/2004 | Brubaker et al. | |
| 6,773,714 B2 | 8/2004 | Dunn et al. | |
| 6,921,541 B2 | 7/2005 | Chasin et al. | |
| 6,974,462 B2 | 12/2005 | Sater | |
| 6,992,110 B2 | 1/2006 | Kranzler et al. | |
| 7,144,412 B2 | 12/2006 | Wolf et al. | |
| 7,166,570 B2 | 1/2007 | Hunter et al. | |
| 7,220,281 B2 | 5/2007 | Lambrecht et al. | |
| 7,229,441 B2 | 6/2007 | Trieu et al. | |

(Continued)

FOREIGN PATENT DOCUMENTS

| | | | |
|---|---|---|---|
| WO | 03005961 | 1/2003 | |
| WO | WO03/044076 A1 * | 5/2003 | 424/426 |

(Continued)

OTHER PUBLICATIONS

Heller et al. "Development of poly(orthoesters) and their application for bovine serum albumin and bupivacaine delivery", Journal of Controlled Release, 78, 133-141. Published Jan. 2002.*
Smith et al. "How to use implantable intrathecal drug delivery systems for refractory cancer pain", The Journal of Supportive Oncology, vol. 1, No. 1. Published May 2003.*
Matot, Idit, et al. "Epidural clonidine, bupivacaine and methadone as the sole analgesic agent after thoracotomy for lung resection", Anaesthesia, 59, 861-866. Published online Aug. 2004.*
Product literature, Atrigel Drug Delivery Platform, Jul. 2006.

(Continued)

*Primary Examiner* — Janet Epps-Smith
*Assistant Examiner* — Audrea Buckley
(74) *Attorney, Agent, or Firm* — Sorell Lenna & Schmidt LLP

(57) ABSTRACT

Effective treatments of dystonia and/or post-stroke spasticity for extended periods of time are provided. Through the administration of an effective amount of clonidine at or near a target site, one can relieve dystonia and/or post-stroke spasticity caused by diverse sources. When appropriate formulations are provided within biodegradable polymers, this relief can be continued for at least five days. In some embodiments, the relief can be for at least twenty-five days, at least fifty days, at least one hundred days, at least one hundred and thirty-five days or at least one hundred and eighty days.

19 Claims, 19 Drawing Sheets

(56) References Cited

U.S. PATENT DOCUMENTS

| | | |
|---|---|---|
| 7,235,043 B2 | 6/2007 | Gellman et al. |
| 7,287,983 B2 | 10/2007 | Ilan |
| 7,318,840 B2 | 1/2008 | McKay |
| 7,329,259 B2 | 2/2008 | Cragg |
| 7,345,065 B2 | 3/2008 | Gil et al. |
| 7,361,168 B2 | 4/2008 | Makower et al. |
| 7,367,978 B2 | 5/2008 | Drewry et al. |
| 7,507,398 B2 | 3/2009 | Rabinowitz et al. |
| 7,524,812 B2 | 4/2009 | Ellis et al. |
| 2002/0009454 A1 | 1/2002 | Boone et al. |
| 2002/0058656 A1 | 5/2002 | Ockert |
| 2002/0090398 A1 | 7/2002 | Dunn et al. |
| 2002/0094998 A1 | 7/2002 | Burke et al. |
| 2003/0022926 A1 | 1/2003 | Lavand'Homme |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0028726 A1 | 2/2004 | Fischer et al. |
| 2004/0072799 A1 | 4/2004 | Li et al. |
| 2004/0082540 A1 | 4/2004 | Ochoa |
| 2004/0101582 A1 | 5/2004 | Wolicki |
| 2004/0109893 A1 | 6/2004 | Chen et al. |
| 2004/0208917 A1 | 10/2004 | Fischer et al. |
| 2004/0214793 A1 | 10/2004 | Ochoa |
| 2004/0265364 A1 | 12/2004 | Ozturk et al. |
| 2005/0058696 A1 | 3/2005 | Donello et al. |
| 2005/0059744 A1 | 3/2005 | Donello et al. |
| 2005/0095277 A1 | 5/2005 | Ozturk et al. |
| 2005/0142163 A1 | 6/2005 | Hunter et al. |
| 2005/0175709 A1 | 8/2005 | Baty, III et al. |
| 2005/0177097 A1* | 8/2005 | Hildebrand et al. ............ 604/66 |
| 2005/0186261 A1 | 8/2005 | Avelar et al. |
| 2005/0197293 A1 | 9/2005 | Mellis et al. |
| 2006/0074422 A1 | 4/2006 | Story et al. |
| 2006/0106361 A1 | 5/2006 | Muni et al. |
| 2006/0148903 A1 | 7/2006 | Burch et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2008/0021074 A1 | 1/2008 | Cartt |
| 2008/0091207 A1 | 4/2008 | Truckai et al. |
| 2008/0152709 A1 | 6/2008 | Bortz |
| 2008/0171075 A1 | 7/2008 | Ozturk et al. |

FOREIGN PATENT DOCUMENTS

| | | |
|---|---|---|
| WO | 2005034998 | 4/2005 |
| WO | 2006011915 A1 | 2/2006 |
| WO | 2006022611 A2 | 3/2006 |
| WO | 2006101540 A1 | 9/2006 |
| WO | 2008079868 A1 | 7/2008 |
| WO | 2009100441 A2 | 8/2009 |

OTHER PUBLICATIONS

Article from Medline, www.medscape.com/viewarticle/552267_3, "Pharmacological Approaches".

Article from eMedicine, Dec. 21, 2007, "Spasticity" by Elizabeth Mohberg-Wolf, pp. 1-15.

Article from PostGraduate Medicine, vol. 104/No. 2/Aug. 1998, "Helping Your Patients With Spasticity Reach Maximal Function" by Daniel P. Moore, MD, pp. 1-9.

U.S. Appl. No. 61/046,269, filed Apr. 18, 2008.

U.S. Appl. No. 12/056,511, filed Mar. 27, 2008.

* cited by examiner

METHODS FOR TREATING CONDITIONS SUCH AS DYSTONIA AND POST-STROKE SPASTICITY WITH CLONIDINE

This application claims the benefit of the filing date of U.S. Provisional Patent Application No. 61/046,201, filed Apr. 18, 2008 and entitled "Clonidine Formulations In A Biodegradable Polymer Carrier" and U.S. Provisional Patent Application No. 61/046,192, filed Apr. 18, 2008 and entitled "Methods for Treating Post-Operative Effects Such as Spasticity and Shivering with Clonidine." The entire disclosures of both of these provisional patent applications are hereby incorporated by reference into the present disclosure.

BACKGROUND OF THE INVENTION

Dystonia is a neurologic movement disorder characterized by sustained muscle contractions, usually producing twisting and repetitive movements or abnormal postures or positions. Almost all dystonic movements share a directional quality that is typically sustained. Movements may be prolonged or occur in an instant. In general, dystonia may be classified based on: the age at which symptoms appear; the area or areas of the body that are affected (anatomical distribution); or the cause of the dystonia.

Cervical dystonia, the most common form of focal dystonia, is characterized by abnormal squeezing and twisting muscle contractions in the head and neck area. The dystonic muscle spasms associated with cervical dystonia (CD) may affect any combination of neck muscles. Sustained muscle contractions result in abnormal positions or posturing of the head and neck which results in considerable pain and discomfort. Periodic or patterned spasms result in jerky head movements or periodic or sustained unnatural positioning of the head (dystonic posturing). Sideways or lateral rotation of the head and twisting of the neck is likely the most common finding in CD. This is known as rotational cervical dystonia. In addition, tilting of the head is often present.

Cervical dystonia may begin in the neck and spread into the shoulders, but the symptoms usually plateau and remain stable within five years of onset. This form of focal dystonia is unlikely to spread beyond the neck and shoulders or become generalized dystonia. Occasionally, people with cervical dystonia develop other focal dystonias.

Cervical dystonia may be primary (meaning that it is the only apparent neurological disorder, with or without a family history) or be brought about by secondary causes such as physical trauma. Cases of inherited cervical dystonia may occur in conjunction with early-onset generalized dystonia, which is associated with the DYT1 gene.

Muscle hypertrophy is present in almost all CD patients. Over two-thirds or up to 80% of patients have associated neck pain. About 33% to 40% of these patients also experience head tremor (i.e., dystonic tremor), hand tremor, or both. Approximately 20% of patients with CD also have blepharospasm or dystonia in other muscles or in muscle groups of the arm or hand. In addition, about 15% of patients have hand tremor resembling essential tremor.

Medical therapies are available for treating dystonia including cervical dystonia, but not all patients get adequate relief. DBS is a surgical procedure that interrupts neuronal circuits in the globus pallidus interna (Gpi) and subthalamic nucleus (STN)—areas of the basal ganglia of the brain that do not work correctly in patients with dystonia. This may lessen patients' symptoms and pain but results in decreased movement. Another treatment is regular botulinum toxin injections to the affected muscle, however, this can result in weakness in the muscle at the site of injection, muscle soreness throughout the body, difficulty swallowing, breathing or talking, double vision and/or hoarseness for several days. In addition, high and frequent doses of botulinum toxin could be fatal as botulinum toxin is made of the same bacterium that causes food poisoning. Also, some oral medications have demonstrated some benefit including anticholinergic drugs such as Artane® (trihexyphenidyl) and Cogentin® (benztropine); dopaninergic drugs such as Sinemet® or Madopar® (levodopa), Parlodel® (bromocriptine), and Symmetrel® (amantadine); and GABAergic drugs such as Valium® (diazepam). However, these medications can have undesirable side effects including central nervous system side effects such as confusion, drowsiness, hallucination, personality change and memory difficulties, and peripheral nervous system side effects such as dry mouth, blurred vision, urinary retention and constipation.

Another debilitating condition is post-stroke spasticity. This can occur after a stroke as certain muscles may start to contract involuntarily. Post-stroke spasticity is characterized by increased muscle tone and resistance to movement. The increased stiffness contributes to fatigue by forcing stroke survivors to expend much more energy to perform basic activities. Complications of inadequately controlled post-stroke spasticity include pain, contractures and decubiti. Up to 30% of stroke survivors suffer this disabling spasticity. Present medical treatments include the use of pharmaceuticals such as baclofen, diazepam and dantrolene. However, these medications often cause sedation in patients or lethargy. Further, some patients experience confusion.

Another treatment for post-stroke spasticity is the use of botulinum toxin A ("Botox"). However, there are many undesirable side effects that can be experienced with the use of Botox as mentioned above. Undesirable side effects of Botox include having trouble breathing, talking, or swallowing; drooping eyelids; unusual or severe muscle weakness (especially in a body area that was not injected with the medication); problems with vision or depth perception; crusting or drainage from your eyes; severe skin rashes or itching; and/or chest pain or a heavy feeling with pain spreading to the arm or shoulder, a general ill feeling.

A pharmaceutical with minimal side effects that is known to the medical profession for treating spasticity due to brain damage is clonidine, which is widely recognized as an antihypertensive agent that acts as an agonist on the alpha-2-adrenergic receptor and a neural receptor agonist. In general, clonidine, also referred to as 2,6-dichloro-N-2-imidazolidinyldenebenzenamine ($C_9H_9Cl_2N_3$), may be represented by the following chemical structure:

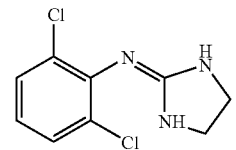

However, to date clonidine has not been widely appreciated as a treatment for conditions such as dystonia and post-stroke spasticity. Thus, there is a need to develop effective formulations of this compound for these applications.

SUMMARY OF THE INVENTION

Compositions and methods are provided comprising clonidine or its pharmaceutically acceptable salts that are administered in order to treat or reduce dystonia and/or post-stroke spasticity.

In one exemplary embodiment, an implantable drug depot for reducing, preventing or treating dystonia and/or post-stroke spasticity in a patient in need of such treatment is provided. The drug depot comprises at least one biodegradeable polymer and clonidine or a pharmaceutically acceptable salt thereof in an amount from about 0.1 wt. % to about 30 wt. % of the drug depot. The drug depot is capable of releasing clonidine over a period of 5 to 135 days. The clonidine or pharmaceutically acceptable salt thereof can be released at an amount between 0.005 and 1.0 mg per day for the period of 5 to 135 days.

In another exemplary embodiment, an implantable drug depot for reducing, preventing or treating dystonia and/or post-stroke spasticity in a patient in need of such treatment is provided, wherein the drug depot comprises at least one biodegradeable polymer and clonidine or a pharmaceutically acceptable salt thereof in an amount from about 0.1 wt. % to about 30 wt. % of the drug depot, and the drug depot releases: (i) a bolus dose of the clonidine; and (ii) an effective amount of the clonidine over a period of at least fifty days.

In another exemplary embodiment, a method for treating dystonia and/or post-stroke spasticity is provided. The method comprises implanting a drug depot in an organism to reduce, prevent or treat dystonia and/or post-stroke spasticity, wherein the drug depot comprises clonidine in an amount from about 0.1 wt. % to about 30 wt. % of the drug depot, and at least one biodegradable polymer. The clonidine is capable of being released in an amount between 0.005 and 1.0 mg per day for a period of 5 to 135 days.

In still another exemplary embodiment, another method for treating dystonia and/or post-stroke spasticity is provided. The method comprises implanting a drug depot in an organism to reduce, prevent or treat dystonia and/or post-stroke spasticity. The drug depot comprises clonidine in an amount from about 0.1 wt. % to about 30 wt. % of the drug depot, and at least one biodegradable polymer. The drug depot is capable of releasing about 5% to about 100% of the clonidine relative to a total amount of the clonidine loaded in the drug depot over a period of 3 to 200 days after the drug depot is implanted in the organism.

In still yet another exemplary embodiment, an implantable drug depot useful for reducing, preventing or treating dystonia and/or post-stroke spasticity in a patient in need of such treatment is provided, wherein the drug depot comprises at least one biodegradeable polymer and a therapeutically effective amount of clonidine, the drug depot is administered at a site to reduce, prevent or treat dystonia and/or post-stroke spasticity, and the drug depot is capable of releasing clonidine at an amount between 0.005 and 1.0 mg per day for a period of 5 to 135 days at the site.

In another exemplary embodiment, there is a sustain release composition comprising an effective amount of clonidine or a pharmaceutically acceptable salt thereof in an implantable drug depot, wherein the clonidine or a pharmaceutically acceptable salt thereof is present in an amount to relieve post-stroke spasticity and/or dystonia for a period of 5 to 135 days and wherein the implantable drug depot facilitates sustain release of clonidine over the period.

In another exemplary embodiment, a method of making an implantable drug depot is provided. The method comprises combining a biocompatible polymer and a therapeutically effective amount of clonidine or pharmaceutically acceptable salt thereof and forming the implantable drug depot from the combination.

Clonidine in the various embodiments may be in the form of a salt. One example of a salt is a hydrochloric salt. In various embodiments, clonidine may be in the form of a base.

In various embodiments, clonidine may be in the form of a mixture of clonidine base and a hydrochloride salt. Further, clonidine or a pharmaceutically acceptable salt thereof may be encapsulated in a plurality of depots comprising microparticles, microspheres, microcapsules, and/or microfibers which could be suspended in a gel. The drug depot may be a pellet.

Clonidine or a pharmaceutically acceptable salt thereof may be present in various embodiments in an amount from about 0.1 wt. % to about 30 wt. % of the drug depot. In some embodiments, clonidine may comprise from about 5 wt. % to about 15 wt. % of the drug depot.

The polymer in various embodiments of this invention comprises one or more of poly(lactide-co-glycolide) (PLGA), polylactide (PLA), polyglycolide (PGA), D-lactide, D,L-lactide, L-lactide, D,L-lactide-co-ϵ-caprolactone, and D,L-lactide-co-glycolide-co-ϵ-caprolactone. Further, the polymer is capable of degrading or degrades in 200 days or less after the drug depot is administered to reduce, prevent or treat dystonia and/or post-stroke spasticity. Also, the polymer may comprise at least about 70% of the total wt. % of the drug depot. In various embodiments, the polymer may comprise poly(lactic-co-glycolic acid) and the poly(lactic-co-glycolic acid) comprises a mixture of polyglycolide and polylactide. The mixture can comprise more polylactide than polyglycolide.

The drug depot in various embodiments is capable of releasing between 0.005 and 3 milligrams (mg) per day of clonidine or pharmaceutically acceptable salt thereof to reduce, prevent or treat dystonia and/or post-stroke spasticity. In some embodiments, the drug depot is capable of releasing between 0.01 and 0.1 mg per day of clonidine or pharmaceutically acceptable salt thereof to reduce, prevent or treat dystonia and/or post-stroke spasticity.

The drug depot in various embodiments may comprise a radiographic marker adapted to assist in radiographic imaging. The radiographic marker may comprise barium, bismuth, tungsten, tantalum, iodine, calcium phosphate and/or metal beads.

The drug depot in various embodiments may comprise at least one additional anti-inflammatory or analgesic agent, at least one anabolic or an anti-catabolic growth factor or a combination thereof.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
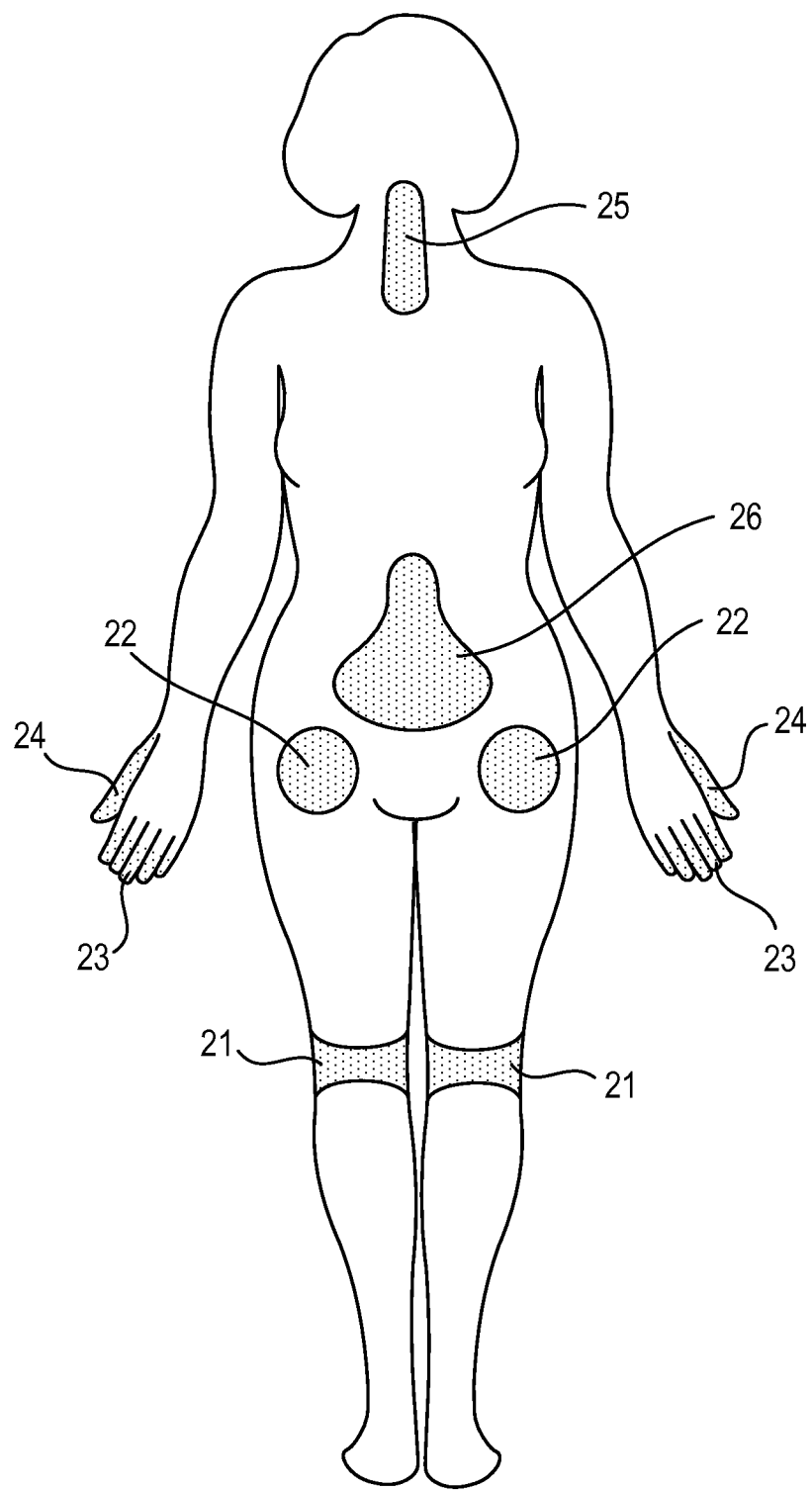
FIG. 1 illustrates a number of common locations within a patient that may be sites at which surgery takes place and locations at which the drug depot containing clonidine can locally be administered thereto and used to treat dystonia and/or post-stroke spasticity.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an" and "the" include plural referents unless expressly and unequivocally limited to one referent. Thus, for example, reference to "a drug depot" includes one, two, three or more drug depots.

A "drug depot" is the composition in which the clonidine is administered to the body. Thus, a drug depot may comprise a physical structure to facilitate implantation and retention in a desired site. The drug depot may also comprise the drug itself. The term "drug" as used herein is generally meant to refer to any substance that alters the physiology of a patient. The term "drug" may be used interchangeably herein with the terms "therapeutic agent," "therapeutically effective amount" and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 5 cm from the administration site and comprises clonidine. A drug depot may also include a pump or pellet.

A "therapeutically effective amount" or "effective amount" is such that when administered, the drug results in alteration of the biological activity, such as, for example, inhibition, reduction or alleviation of dystonia and/or post-stroke spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments, the formulation is designed for immediate release. In other embodiments, the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible," it is meant that the depot will erode or degrade over time due, at least in part, to contact with substances found in the surrounding tissue, fluids or by cellular action. By "bioabsorbable," it is meant that the depot will be broken down and absorbed within the human body, for example, by a cell or tissue. "Biocompatible" means that the depot will not cause substantial tissue irritation or necrosis at the target tissue site.

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The two types of formulations (sustain release and immediate release) may be used in conjunction. The sustained release and immediate release may be in one or more of the same depots. In various embodiments, the sustained release and immediate release may be part of separate depots. For example, a bolus or immediate release formulation of clonidine may be placed at or near the target site and a sustain release formulation may also be placed at or near the same site. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four to seventy-two hours after implantation. "Initial burst" or "burst effect" or "bolus dose" refers to the release of therapeutic agent from the depot during the first twenty-four hours to seventy-two hours after the depot comes in contact with an aqueous fluid (e.g., synovial fluid, cerebral spinal fluid, etc.). The "burst effect" is believed to be due to the increased release of therapeutic agent from the depot. In alternative embodiments, the depot (e.g., gel) is designed to avoid or reduce this initial burst effect (e.g., by applying an outer polymer coating to the depot).

"Treating" or "treatment" of a disease or condition refers to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing as well as after their appearance. Thus, treating or treatment includes preventing or prevention of disease or undesirable condition. In addition, treating or treatment does not require complete alleviation of signs or symptoms, does not require a cure, and specifically includes protocols that have only a marginal effect on the patient. "Reducing dystonia and/or post-stroke spasticity" includes a decrease in symptoms of dystonia or post-stroke spasticity and does not require complete alleviation of dystonia or post-stroke spasticity signs or symptoms, and does not require a cure. In various embodiments, reducing dystonia or post-stroke spasticity includes even a marginal decrease in dystonia or post-stroke spasticity. By way of example, the administration of the effective dosage of clonidine may be used to prevent, treat or relieve the symptoms of dystonia and/or post-stroke spasticity.

The term "implantable" as utilized herein refers to a biocompatible device (e.g., drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a nerve root of the nervous system or a region of the brain, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, e.g., mcg/hr, mcg/day, 10% per day for ten days, etc. As persons of ordinary skill know, a release rate profile may, but need not, be linear. By way of a non-limiting example, the drug depot may be a pellet that releases the clonidine over a period of time (see FIGS. 5-34).

The term "solid" is intended to mean a rigid material, while, "semi-solid" is intended to mean a material that has some degree of flexibility, thereby allowing the depot to bend and conform to the surrounding tissue requirements.

"Targeted delivery system" provides delivery of one or more drugs depots, gels or depots dispersed in the gel having a quantity of therapeutic agent that can be deposited at or near the target site as needed for treatment of pain, inflammation or other disease or condition.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "POE" refers to poly(orthoester).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Clonidine

When referring to clonidine, unless otherwise specified or apparent from context, it is understood that the inventors are also referring to pharmaceutically acceptable salts. One well-known commercially available salt for clonidine is its hydrochloride salt. Some other examples of potentially pharmaceutically acceptable salts include those salt-forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to clonidine, the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non limiting example, when formulating clonidine with poly(orthoesters) it may be desirable to use the clonidine base formulation. By contrast, when formulating clonidine with PLGA, it may be desirable to use the HCl salt form. In some embodiments, clonidine may be incorporated into a polymer core with a polymer and then coated with the same or different polymer.

The clonidine or its pharmaceutically acceptable salt may be administered with a muscle relaxant. Exemplary muscle relaxants include by way of example and not limitation, alcuronium chloride, atracurium bescylate, baclofen, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium or combinations thereof.

The drug depot may comprise other therapeutic agents in addition to the clonidine as well. These therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10 or HuMax IL-15 (anti-IL 15 antibodies).

Other suitable therapeutic agents include IL-1 inhibitors, such Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression) and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as glucocorticoids, antioxidants such as dithiocarbamate, and other compounds, such as, for example, sulfasalazine.

Examples of therapeutic agents suitable for use also include but are not limited to an anti-inflammatory agent, an analgesic agent, or an osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[–4-[C2-pyridinylamino)sulfonyl]azo]benzoic acid, sulindac, tepoxalin or tolmetin; as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include but are not limited to a bone morphogenetic protein, a growth differentiation factor, a LIM mineralization protein, CDMP or progenitor cells or a combination thereof.

Suitable analgesic agents include but are not limited to acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin or a combination thereof.

The clonidine may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

Exemplary excipients that may be formulated with clonidine in addition to the biodegradable polymer include but are not limited to MgO (e.g., 1 wt. %), 5050 DLG 6E (Lakeshore Biomaterials, Birmingham, Ala.), 5050 DLG 1A (Lakeshore Biomaterials, Birmingham, Ala.), mPEG, TBO-Ac, mPEG, Span-65, Span-85, pluronic F127, TBO-Ac, sorbitol, cyclodextrin, maltodextrin, pluronic F68, CaCl, 5050 DLG-7A (Lakeshore Biomaterials, Birmingham, Ala.) and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 50 wt. % of the formulation. In some embodiments, the excipients comprise from about 0.001 wt. % to about 2 wt. % of the formulation.

In various embodiments, the non-active ingredients will be durable within the tissue site for a period of time equal to or greater than (for biodegradable components and non-biodegradable components) the planned period of drug delivery.

In some embodiments, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s). Non-biodegradable polymers include but are not limited to PVC and polyurethane.

In some embodiments, the drug depot may not be fully biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics, methacrylates, poly (N-isopropylacrylamide), PEO-PPO-PEO (pluronics) or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bio-erodible, a bioabsorbable, and/or a biodegradable biopolymer that may provide immediate release or sustained release of the clonidine. Examples of suitable sustained release biopolymers include but are not limited to poly(alpha-hydroxy acids), poly(lactide-co-glycolide), polylactide, polyglycolide (PG), D-lactide, D,L-lactide, L-lactide, D,L-lactide-co-ε-caprolactone, D,L-lactide-co-glycolide-co-ε-caprolactone, polyhydroxybutyrate, poly(glycolide-co-trimethylenecarbonate), poly(lactic acid-co-lysine), poly(lactide-co-urethane), poly(ester-co-amide), PEG conjugates of poly (alpha-hydroxy acids), poly(orthoester)s, polyaspirins, polyphosphazenes, polyanhydrides; polyketals, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, ε-caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG tri-block copolymers, SAIB (sucrose acetate isobutyrate) or combinations thereof. As persons of ordinary skill are aware, mPEG may be used as a plasticizer for PLGA, but other polymers/excipients may be used to achieve the same effect.

mPEG imparts malleability to the resulting formulations. In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

As persons of ordinary skill in the art are aware, when an implantable depot composition having a blend of polymers with different end groups is used, the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer), there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

The depot can be of different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a pellet, a flat surface such as a disc, film or sheet (e.g., ribbon-like) or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 4 mm. In various embodiments, as the diameter decreases, the surface area that comes in contact with the bodily fluid of the depot increases and therefore release of the drug from the depot increases. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten and/or metal beads or particles. In various embodiments, the radiographic marker could be a spherical shape or a ring around the depot.

FIG. 1 illustrates a number of common locations within a patient that may be sites at which the clonidine may be administered. It will be recognized that the locations illustrated in FIG. 1 are merely exemplary of the many different locations at which clonidine can be administered. For example, administration may be required at a patient's knees 21, hips 22, fingers 23, thumbs 24, neck 25 and/or spine 26.

Gel

In various embodiments, the clonidine is administered in a gel. The gel may have a pre-dosed viscosity in the range of about 1 to about 2000 centipoise (cps), 1 to about 200 cps, or 1 to about 100 cps. After the gel is administered to the target site, the viscosity of the gel will increase and the gel will have a modulus of elasticity (Young's modulus) in the range of about $1 \times -10^2$ to about $6 \times 10^5$ dynes/cm$^2$, $2 \times 10^4$ to about $5 \times 10^5$ dynes/cm$^2$, or $5 \times 10^4$ to about $5 \times 10^5$ dynes/cm$^2$.

In one embodiment, a depot comprises an adherent gel comprising clonidine that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times -10^2$ to about $3 \times 10^5$ dynes/cm$^2$, $2 \times 10^4$ to about $2 \times 10^5$ dynes/cm$^2$ or $5 \times 10^4$ to about $1 \times 10^5$ dynes/cm$^2$. The post-dosed hardening gels (after delivery) may have a rubbery consistency and have a modulus of elasticity in the range of about $1 \times -10^2$ to about $2 \times 10^6$ dynes/cm$^2$, $1 \times 10^5$ to about $7 \times 10^5$ dynes/cm$^2$ or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The choice of method to vary molecular weight is typically determined by the composition of the gel (e.g., polymer versus non-polymer). For example, in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different MWs, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In some embodiments, when the polymer materials have different chemistries (e.g., high MW DLG 5050 and low MW DL), the high MW polymer may degrade faster than the low MW polymer.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides or a combination thereof. Synthetic hydrogels include but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly (N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane or a combination thereof.

In various embodiments, rather than directly admixing the therapeutic agent into the gel, microspheres may be dispersed within the gel, the microspheres being loaded with clonidine. In one embodiment, the microspheres provide for a sustained release of the clonidine. In yet another embodiment, the gel, which is biodegradable, prevents the microspheres from releasing the clonidine; the microspheres thus do not release the clonidine until they have been released from the gel. For example, a gel may be deployed around a target tissue site (e.g., a nerve root). Dispersed within the gel may be a plurality of microspheres that encapsulate the desired therapeutic agent. Certain of these microspheres degrade once released from the gel, thus releasing the clonidine.

Microspheres, much like a fluid, may disperse relatively quickly, depending upon the surrounding tissue type, and hence disperse the clonidine. In some situations, this may be desirable; in others, it may be more desirable to keep the clonidine tightly constrained to a well-defined target site. The present invention also contemplates the use of adherent gels to so constrain dispersal of the therapeutic agent. These gels may be deployed, for example, in a disc space, in a spinal canal or in surrounding tissue.

Drug Delivery

It will be appreciated by those with skill in the art that the depot can be administered to the target site using a "cannula" or "needle" that can be a part of a drug delivery device, e.g., a syringe, a gun drug delivery device or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes but is not limited to from about 0.05 to about 1.655 (mm). The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include but are not limited to barium, bismuth, tantalum, tungsten, iodine, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which requires individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including but not limited to gas sterilization, such as, for example, with ethylene oxide or steam sterilization.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering a therapeutic agent into a site of a patient is provided, the method comprising inserting a cannula at or near a target tissue site and implanting the drug depot at the target site beneath the skin of the patient and brushing, dripping, injecting, or painting the gel in the target site to hold or have the drug depot adhere to the target site. In this way, unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered at or near the target site. In those embodiments, where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Figure 2:
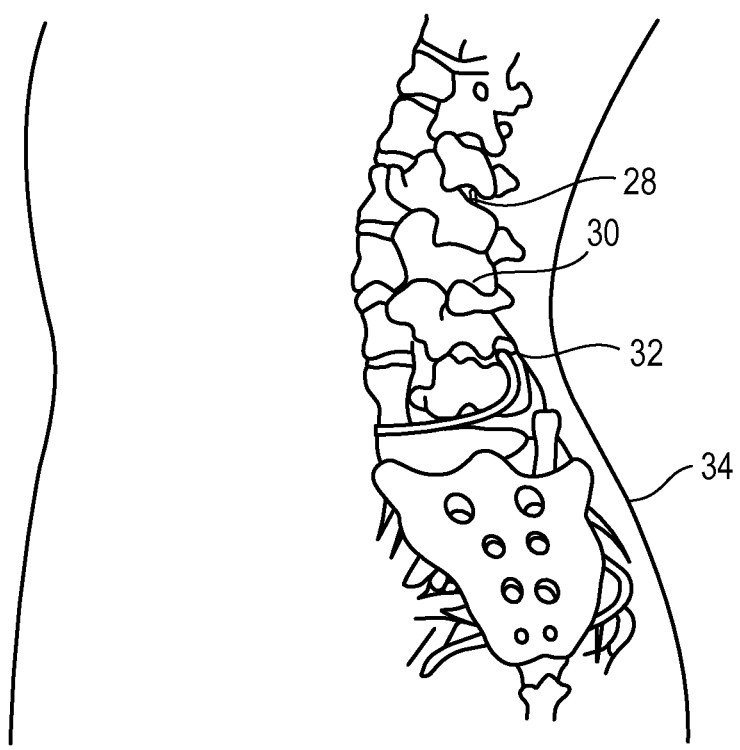
FIG. 2 illustrates a schematic dorsal view of the spine and sites where the drug depot containing clonidine can locally be administered thereto.

One exemplary embodiment where the depot is suitable for use in treating post-stroke spasticity is illustrated in FIG. 2. Schematically shown in FIG. 2 is a dorsal view of the spine 30 and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including but not limited to at least one muscle, ligament, tendon, the cervical part of the spine, cartilage, a spinal disc, a spinal foraminal space, near the spinal nerve root and the spinal canal.

In some embodiments, it is preferable to co-administer clonidine with an antagonist to counteract undesirable effects, for example, the blood pressure decrease that can be caused by clonidine. Exemplary antagonists include but are not limited to phentolamine, yohimbine, tolazoline and piperoxane. Additionally, compounds such as 5-fluorodeoxyuridine (FUDR) and 3,4 dehydroprolene may also be included. These compounds may prevent or reduce glial and fibroblastic scar formation associated with some types of surgeries.

The clonidine-based formulation of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, saline solution, gelatin, lactose, starches, stearic acid, magnesium stearate, sicaryl alcohol, talc, vegetable oils, benzyl alcohols, gums, waxes, propylene glycol, polyalkylene glycols and other known carriers for medicaments.

Parenteral administration may additionally include, for example, an infusion pump that administers a pharmaceutical composition (e.g., analgesic and anti-inflammatory combination) through a catheter near the spine or one or more inflamed joints, an implantable mini-pump that can be inserted at or near the target site, an implantable controlled release device or sustained release delivery system that can release a certain amount of the statin per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas that provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, continually, at specific times, or at set intervals between deliveries.

Another embodiment is directed to a method for treating a mammal suffering from dystonia and/or post-stroke spasticity, the method comprising administering a therapeutically effective amount of clonidine at a target site beneath the skin. The clonidine (or pharmaceutically acceptable salt) may for example be administered locally to the target tissue site as a drug depot.

In some embodiments, the clonidine is suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

In various embodiments, the drug depot comprising the clonidine can be made by combining a biocompatible polymer and a therapeutically effective amount of clonidine or pharmaceutically acceptable salt thereof and forming the implantable drug depot from the combination.

Various techniques are available for forming at least a portion of a drug depot from the biocompatible polymer(s), therapeutic agent(s) and optional materials including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: clonidine and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: clonidine, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, clonidine may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding a biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is pre-compounded with a radiographic agent (e.g., radio-opacifying agent) under conditions of temperature and mechanical shear that would result in substantial degradation of the therapeutic agent, if it were present. This pre-compounded material is then mixed with a therapeutic agent under conditions of lower temperature and mechanical shear, and the resulting mixture is shaped into the clonidine containing drug depot. Conversely, in another embodiment, the biocompatible polymer can be pre-compounded with the therapeutic agent under conditions of reduced temperature and mechanical shear. This pre-compounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of clonidine because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as clonidine is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, clonidine is used and mixed or sprayed with the PLGA or PEG550 polymer, and the resulting depot may be formed by extrusion and dried.

In various embodiments, there is a pharmaceutical formulation comprising: clonidine, wherein the clonidine comprises from about 0.1 wt. % to about 30 wt. % of the formulation, and at least one biodegradable polymer. In some embodiments, the clonidine comprises from about 3 wt. % to about 20 wt. %, about 3 wt. % to about 18 wt. %, about 5 wt. % to about 15 wt. % or about 7.5 wt. % to about 12.5 wt. % of the formulation. By way of an example, when using a 5%-15% clonidine composition, the mole ratio of clonidine to polymer would be from approximately 16-53 when using an approximately 80 kDalton polymer that has a 267 grams/mole ratio. By way of another example, when using a 5%-15% clonidine base in the composition, the mole ratio of clonidine base to polymer would be from approximately 18-61 with a mole mass of 230 g/mol.

In some embodiments, the drug depot comprises at least one biodegradable material in a wt. % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, the at least one biodegradable polymer comprises poly(lactic-co-glycolide), poly(orthoester) or a combination thereof. The poly(lactic-co-glycolide) may comprise a mixture of polyglycolide and polylactide and in some embodiments, in the mixture, there is more polylactide than polyglycolide. In various embodiments, there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; or 0% polylactide and 100% polyglycolide.

In various embodiments that comprise both polylactide and polyglycolide, there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, the drug particle size (e.g., clonidine) is from about 5 to 30 micrometers, however, in various embodiments ranges from about 1 micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the clonidine are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 200 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, there is a pharmaceutical formulation comprising clonidine, wherein the clonidine is in a mixture of clonidine hydrochloride and clonidine base and the mixture comprises from about 0.1 wt. % to about 30 wt. % of the formulation and a polymer comprises at least 70% of the formulation. In some embodiments, the polymer in this formulation is polyorthoester.

In some embodiments, the formulation comprises a drug depot that comprises a biodegradable polyorthoester. The mechanism of the degradation process of the polyorthoester can be hydrolytical or enzymatical in nature, or both. In various embodiments, the degradation can occur either at the surface of the drug depot (heterogeneous or surface erosion) or uniformly throughout the drug delivery system depot (homogeneous or bulk erosion). Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, there are methods for treating dystonia and/or post-stroke spasticity. These methods comprise: administering a pharmaceutical composition to an organism, wherein the pharmaceutical composition comprises from about 0.1 wt. % to about 30 wt. % of the formulation, and at least one biodegradable polymer. In some embodiments, the loading is from about 1 wt. % to about 25 wt. %, or about 5 wt. % to about 10 wt. %. In some embodiments, the loading is from about 10 wt. % to about 20 wt. %.

In some embodiments, there is a higher loading of clonidine, e.g., at least 20 wt. %, at least 30 wt. %, at least 40 wt. %, at least 50 wt. %, at least 60 wt. %, at least 70 wt. %, at least 80 wt. % or at least 90 wt. %.

A strategy of triangulation may be effective when administering these pharmaceutical formulations. Thus, a plurality (at least two, at least three, at least four, at least five, at least six, at least seven, etc.) of drug depots comprising the pharmaceutical formulations may be placed around the target site such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as mort and pestle, jet-drying or jet milling.

In some embodiments, clonidine is released at a rate of 2-3 µg per day for a period of at least three days. In some embodiments, this release rate continues for at least ten days, at least fifteen days, at least twenty-five days, at least fifty days, at least ninety days, at least one hundred days, at least one-hundred and thirty-five days, at least one-hundred and fifty days or at least one hundred and eighty days. For some embodiments, 300-425 micrograms of clonidine as formulated with a biopolymer are implanted into a person at or near a target tissue site. If clonidine is implanted at multiple sites that triangulate the target site, then in some embodiments, the total amount of clonidine at each site is a fraction of the total 300-425 micrograms. For example, one may implant a single dose of 324 micrograms at one site, or two separate doses of 162 micrograms at two sites, or three separate doses of 108 micrograms at three sites that triangulate the tissue site. It is important to limit the total dosage to an amount less than that which would be harmful to the organism. However, in some embodiments, although when there are a plurality of sites each site may contain less than the total dose that might have been administered in a single application, it is important to remember that each site will independently have a release profile, and the biopolymers' concentration and substance should be adjusted accordingly to ensure that the sustain release occurs over sufficient time.

The dosage may be from approximately 0.0005 to approximately 960 µg/day. Additional dosages of clonidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 µg/day. In another embodiment, the dosage of clonidine is from approximately 0.005 to approximately 2.5 µg/day. In some embodiments, the amount of clonidine is between 40 and 600 µg/day. In some embodiments, the amount of clonidine is between 200 and 400 µg/day.

In some embodiments, the therapeutically effective dosage amount (e.g., clonidine dose) and the release rate profile are sufficient to reduce dystonia and/or post-stroke spasticity for a period of at least one day, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 135 days, 3 days to 180 days, or 3 days to 6 months or 1 year or longer.

In some embodiments, the clonidine depot is designed for a bolus dose or burst dose within 1, 2 or 3 days after implantation to provide an immediate release of the clonidine for treatment of dystonia and/or post-stroke spasticity.

In some embodiments, the clonidine depot is administered parenterally, e.g., by injection. In some embodiments, the injection is intrathecal, which refers to an injection into the spinal canal (intrathecal space surrounding the spinal cord). An injection may also be into a muscle or other tissue. In other embodiments, the clonidine depot is administered by placement into an open patient cavity during surgery.

In some embodiments, the drug depot (i) comprises one or more immediate release layer(s) that is capable of releasing about 5% to about 20% of the clonidine or pharmaceutically acceptable salts thereof relative to a total amount of the clonidine or pharmaceutically acceptable salt thereof loaded in the drug depot over a first period of up to 48 hours and (ii) one or more sustain release layer(s) that is capable of releasing about 21% to about 99% of the clonidine or pharmaceutically acceptable salt thereof relative to a total amount of the clonidine or pharmaceutically acceptable salt thereof loaded in the drug depot over a subsequent period of up to 3 days to 90 days, 150 days, 180 days or 6 months to 1 year.

In one exemplary dosing regimen, a rat may be provided with sufficient clonidine in a biodegradable polymer to provide sustain release of 0.240 μg/day for 135 days. The total amount of clonidine that is administered over this time period would be approximately 32.4 μg. In another exemplary dosing regimen, a human is provided with sufficient clonidine in a biodegradable polymer to provide sustain release of 2.4 μg/day for 135 days. The total amount of clonidine that is administered over this time period would be approximately 324 μg.

When using a plurality of pellets, the pellet number is based on the amount of drug loading into a pellet of appropriate size (i.e., 0.5 mm diameter×4 mm length) and how much drug is needed (e.g., approximately 325 μg clonidine (3 pellets)). In some embodiments, there is a polymer that releases a bolus amount of compound over the first few (~5) days before it settles down and releases 2.5 mg/day for 135 days. An exemplary formulation is 5 wt. % clonidine, 100 DL 5E (Lakeshore Biomaterials, Birmingham, Ala.).

In some embodiments, the polymer depots of the present invention enable one to provide efficacy of the active ingredient that is equivalent to subcutaneous injections that deliver more than 2.5 times as much drug.

Having now generally described the invention, the same may be more readily understood through the following reference to the following examples, which are provided by way of illustration and are not intended to limit the present invention unless specified.

EXAMPLES

The examples below show certain particularly advantageous results wherein the initial burst is not too large (i.e., not more than 7% of the load drug in the first five days) and the daily dose is approximately 2.4 μg/day±0.5 μg/day for 135 days. See e.g., FIGS. 12, 13, 14 and 19. The figures further demonstrate that drug loadings 5 wt. % to 8 wt. % provide advantageous results.

A 2-month chronic constriction injury (CCI) model of neuropathic pain was used to evaluate different formulations of clonidine encapsulated in bioerodible polymers compared to clonidine given subcutaneously (SC). Different formulations as provided in Table 5 below were evaluated for reducing pain-associated behaviors: Thermal paw withdrawal latency was evaluated at baseline, 7, 14, 21, 28, 35, 42, 49, 56 and 64 days post-operatively, while mechanical threshold was evaluated at 8, 15, 22, 29, 36, 43, 50, 57 and 64 days post-operatively. Bar graphs depicting the results of theses tests are shown in FIGS. 3-4.

Figure 3:
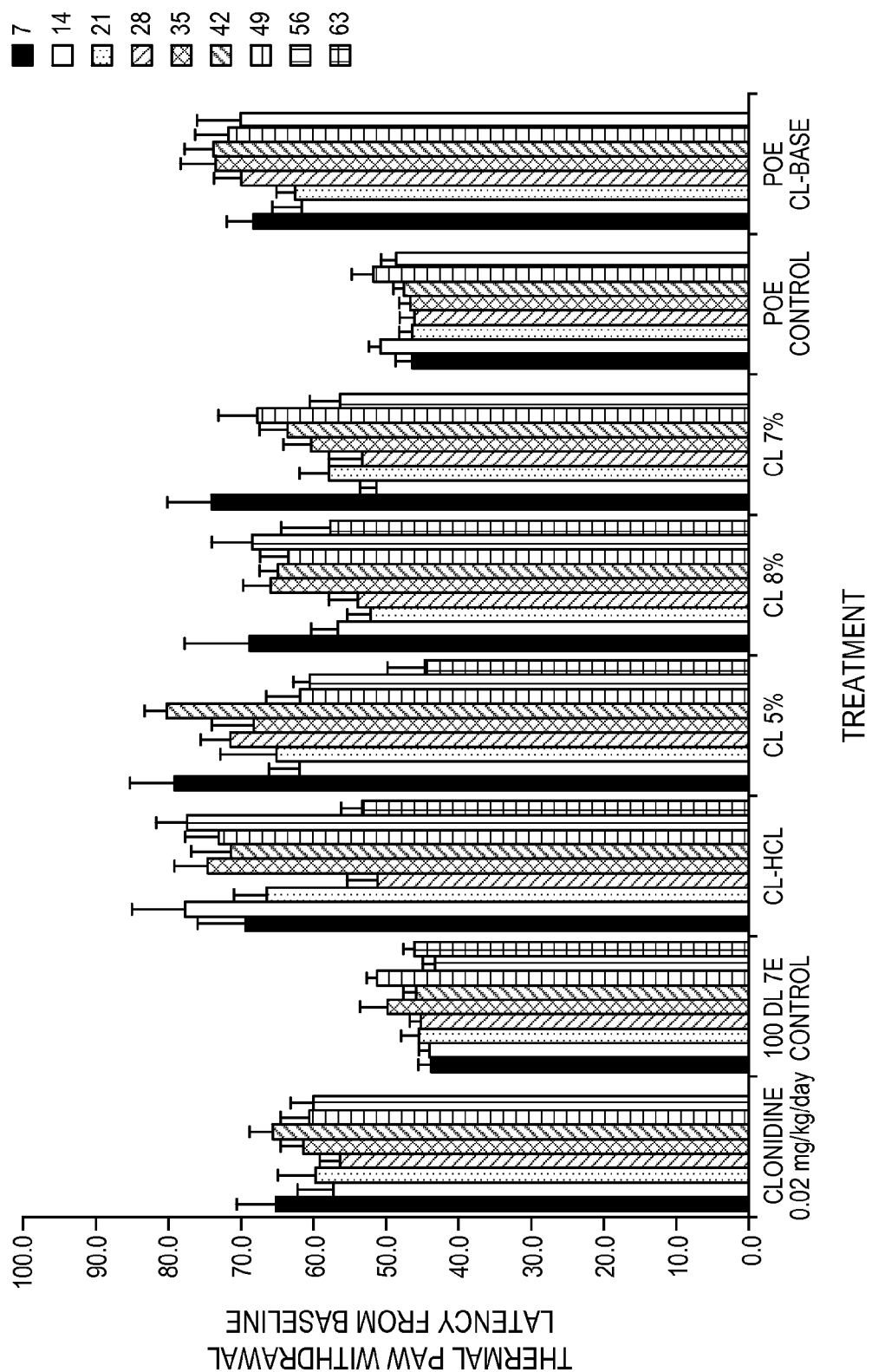
FIG. 3 is a graphic representation of the thermal paw withdrawal latency as a percentage from baseline for the following administrations: clonidine 0.02 mg/kg/day subcutaneously, 100 DL 7E Control, 5% CL-HCL, CL 5%, CL 8%, 1 CL 7%, POE Control and POE CL-Base, at 7 days, 14 days, 21 days, 28 days, 35 days, 42 days, 49 days, 56 days and 63 days. CL-HCL refers to clonidine hydrochloride. "POE" refers to poly(orthoester). "CL-Base" refers to clonidine in its base form.

FIG. 3 is a graphic representation of the thermal paw withdrawal latency as a percentage from baseline for the following administrations: clonidine 0.02 mg/kg/day subcutaneously, 100 DL 7E Control, 5% CL-HCL, CL 5%, CL 8%, 1 CL 7%, POE Control and POE CL-Base, at 7 days, 14 days, 21 days, 28 days, 35 days, 42 days, 49 days, 56 days and 63 days. CL-HCL refers to clonidine hydrochloride. "POE" refers to poly(orthoester). "CL-Base" refers to clonidine in its base form. The clonidine formulations reduced the pain threshold in the animals tested.

Figure 4:
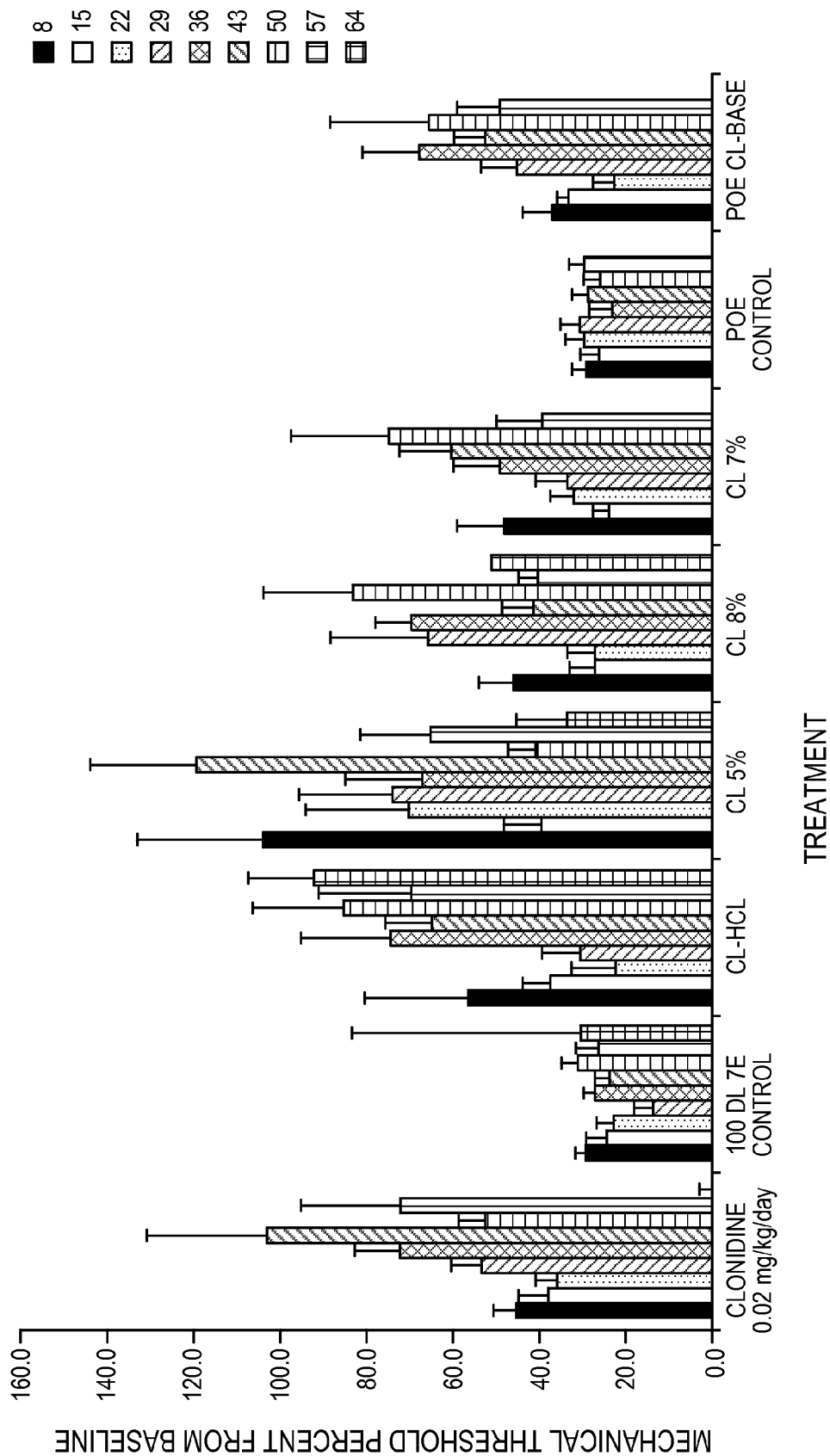
FIG. 4 is a graphic representation of the mechanical threshold as a percentage from baseline for the following administrations: clonidine 0.02 mg/kg/day subcutaneously, 100 DL 7E Control, 5% CL-HCL, CL 5%, CL 8%, CL 7%, POE Control and POE CL-Base, at 8 days, 15 days, 22 days, 29 days, 36 days, 43 days, 50 days, 57 days and 64 days.

FIG. 4 is a graphic representation of the mechanical threshold as a percentage from baseline for the following administrations: clonidine 0.02 mg/kg/day subcutaneously, 100 DL 7E Control, 5% CL-HCL, CL 5%, CL 8%, CL 7%, POE Control and POE CL-Base, at 8 days, 15 days, 22 days, 29 days, 36 days, 43 days, 50 days, 57 days and 64 days. The clonidine formulations reduced the pain threshold in the animals tested.

In Vitro elution studies were carried out at 37° C. in phosphate-buffered saline (PBS, pH 7.4). Briefly, the rods (n=3) were weighed prior to immersion in 5 mL of PBS. At regular time intervals, the PBS was removed for analysis and replaced with 5 mL of fresh PBS. The PBS-elution buffer was analyzed for clonidine content using UV-Vis spectrometry.

Example 1

Formulation Testing

The inventors prepared a number of clonidine formulations in which they varied the polymer type, drug load, excipient (including some formulations in which there was no excipient), pellet size and processing. These formulations are described below in Table 1, Table 2 and Table 3. A number of tests were performed on these formulations, including in vitro release tests in which the number of micrograms released was measured, as well as the cumulative percentage release of clonidine. The results of these tests appear in FIGS. 5-36.

Figure 5:
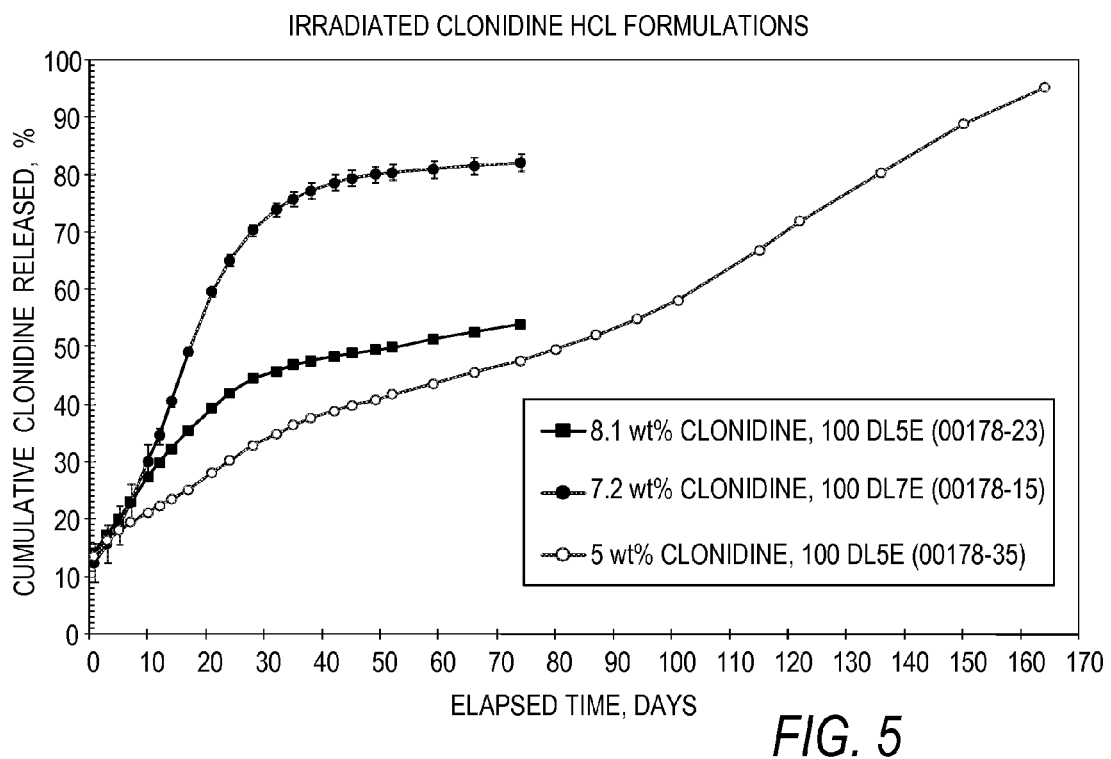
FIG. 5 is a graphic representation of an in vitro release of clonidine from three pellet doses as measured by percentage release.

FIG. 5 is a graphic representation of a study of the cumulative release by percentage of clonidine HCl sterilized formulations for an in vivo efficacy study mentioned in FIGS. 3 and 4. In FIG. 5, the formulations (first three of Table 3) contained: 8.1 wt. % clonidine, the remainder 100 DL 5E (the inherent viscosity of the 100 DL was 0.45-0.55 and had an ester end group), or 7.2 wt. % clonidine, the remainder 100 DL 7E (the inherent viscosity of the 100 DL was 0.60-0.80 and had an ester end group) or 5 wt. % clonidine, the remainder 100 DL 5E (the inherent viscosity of the 100 DL was 0.45-0.55 and had an ester end group). The formulations with the higher drug loads released the fastest over 70 days, with a cumulative release of 45% and 80%. The formulation with 5% clonidine drug load released drug the longest for over 160 days and had a cumulative release of 95% of the drug.

Figure 6:
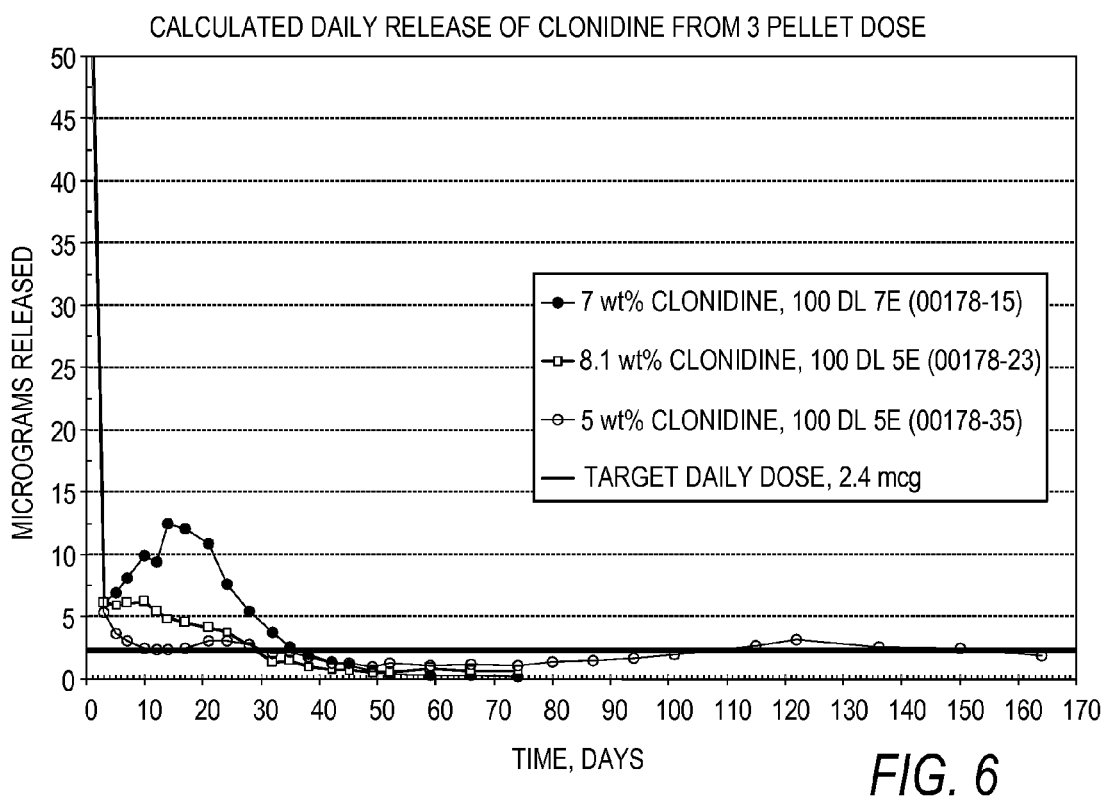
FIG. 6 is a graphic representation of the calculated daily release of clonidine from three pellet doses as measured by micrograms released in vitro.

FIG. 6 is an in vitro graphic representation of studies of the percentage daily release profiles of sterilized clonidine formulations of FIG. 5 (first three of Table 3) and their cumulative average daily release of the three formulations in micrograms per day. Each drug depot had an initial burst effect with a release of clonidine over 50 mcg for the first day. These calculations are based on 3 pellets implanted (which would approximate the dose of clonidine in humans). The pellets ranged in size from 0.5 mm to about 1 mm in diameter and 3-4 mm in length, which would be small enough to place in a needle. The formulations with the higher drug loads released the fastest over 70 days, where the drug dose released was about 5 mcg to about 0.1 mcg/day after about the first 30 days and the formulation with the lowest drug load of about 5% clonidine released the longest for a period of over 160 days, where the release was consistently between about 5 mcg to 0.1 mcg/day after about day 30. The target daily dose was 2.4 mcg/day and the formulation with the 5% clonidine drug load came closest to this target daily dose.

In vitro elution studies were carried out at 37° C. in phosphate-buffered saline (PBS, pH 7.4). The rods (n=3) were weighed prior to immersion in 5 mL of PBS. At regular time intervals, the PBS was removed for analysis and replaced with 5 mL of fresh PBS. The PBS-elution buffer was analyzed for clonidine content using UV-Vis spectrometry.

TABLE 1

| Notebook ID | Polymer Type | Drug Load (Wt. %) | Excipient | Pellet Size (L × Dia; mm) or Description | Processing |
|---|---|---|---|---|---|
| 13335-60-1 | 8515 DLG 7E | 10 | N/A | 0.75 × 0.75 | Melt extrusion, co-spray dried drug/polymer |
| 13335-60-2 | 8515 DLG 7E | 10 | N/A | 0.75 × 0.75 | Melt extrusion, spray dried drug |
| 13335-60-3 | 8515 DLG 7E | 10 | N/A | 0.75 × 0.75 | Melt extrusion, hand ground drug |
| 13335-60-4 | 8515 DLG 7E | 10 | N/A | 0.75 × 0.75 | Melt extrusion, hand ground drug, spray dried polymer |
| 13335-60-5 | 8515 DLG 7E | 10 | N/A | 0.75 × 0.75 | Melt extrusion w/ recycle loop, hand ground drug |
| 13335-65-1 | 8515 DLG 7E | 5 | N/A | 3.0 × 0.75 | Melt extrusion, spray dried drug |
| 13335-65-2 | 8515 DLG 7E | 10 | N/A | 1.5 × 0.75 | Melt extrusion, spray dried drug |
| 13335-65-3 | 8515 DLG 7E | 20 | N/A | 0.75 × 0.75 | Melt extrusion, spray dried drug |
| 13335-65-4 | 100 DL 7E | 5 | N/A | 3.0 × 0.75 | Melt extrusion, spray dried drug |
| 13335-65-5 | 100 DL 7E | 10 | N/A | 1.5 × 0.75 | Melt extrusion, spray dried drug |
| 13335-65-6 | 100 DL 7E | 20 | N/A | 0.75 × 0.75 | Melt extrusion, spray dried drug |
| 13335-97-1 | 8515 DLG 7E | 7.5 | N/A | 3.0 × 0.75 | Melt extrusion, spray dried drug |
| 13335-97-2 | 100 DL 7E | 5 | N/A | 3.0 × 0.75 | Melt extrusion, spray dried drug |
| 13335-97-3 | 8515 DLG 7E | 5 | 10% mPEG | 3.0 × 0.75 | Melt extrusion, spray dried drug |
| 13335-97-4 | 100 DL 7E | 5 | 10% mPEG | 3.0 × 0.75 | Melt extrusion, spray dried drug |
| 13699-1-1 | 100 DL 7E | 5 | N/A | 3.0 × 0.75 | Melt extrusion, spray dried drug |
| 13699-16-1 | 8515 DLG 7E | 10 | N/A | 1.5 × 0.75 | Melt extrusion, spray dried drug |
| 13699-16-2 | 9010 DLG 7E | 10 | N/A | 1.5 × 0.75 | Melt extrusion, spray dried drug |
| 13699-16-3 | 9010 DLG 7E | 5 | N/A | 3.0 × 0.75 | Melt extrusion, spray dried drug |
| 13699-16-4 | 8515 DLG 7E | 5 | 5% mPEG | 3.0 × 0.75 | Melt extrusion, spray dried drug |
| 13699-16-5 | 8515 DLG 7E | 5 | 2.5% mPEG | 3.0 × 0.75 | Melt extrusion, spray dried drug |
| 13699-20-1 | 8515 DLG 7E | 5 | 1% MgO | 3.0 × 0.75 | Melt extrusion, spray dried drug |
| 13699-20-4 | 8515 DLG 7E | 5 | N/A | 3.0 × 0.75 | Melt extrusion, spray dried drug |
| 13699-20-5 | 100 DL 7E | 5 | 10% 5050 DLG 6E | 3.0 × 0.75 | Melt extrusion, spray dried drug |
| 13699-20-6 | 100 DL 7E | 5 | 10% 5050 DLG 1A | 3.0 × 0.75 | Melt extrusion, spray dried drug |
| 13699-20-7 | 8515 DLG Purac | 10 | N/A | 1.5 × 0.75 | Melt extrusion, spray dried drug |
| 13699-20-8 | 8515 DLG 7E | 5 | N/A | 3.0 × 0.75 | Melt extrusion 2X, spray dried drug |
| 13699-28-1 | 8515 DLG Purac | 7.5 | N/A | 3.0 × 0.75 | Melt extrusion, spray dried drug |
| 13699-28-2 | 8516 DLG Purac | 12.5 | N/A | 2.0 × 0.75 | Melt extrusion, spray dried drug |
| 13699-28-3 | 100 DL 7E | 5 | N/A | 3.0 × 0.75 | Melt extrusion, spray dried drug |
| 13699-31-1 | 8515 DLG 7E | 10 | N/A | N/A | heat press, spray dried drug |
| 13699-31-2 | 8515 DLG 7E | 10 | N/A | N/A | heat press, spray dried drug |
| 13699-31-3 | 8515 DLG 7E | 10 | N/A | N/A | heat press, spray dried drug |
| 13699-31-4 | 8515 DLG 7E | 10 | N/A | N/A | Melt extrusion, spray dried drug |
| 12702-13-4-a | 1,6-Hexanediol/tCHDM | 10 | N/A | 3 × 3 | Melt extrusion |
| 12702-13-4-b | 75/25 PLGA | 10 | N/A | 3 × 3 | Melt extrusion |
| 12702-68-12 | 75/25 PLGA | 5 | mPEG | 1 × 1 | Melt extrusion |
| 12702-68-13 | 75/25 PLGA | 5 | TBO-Ac | 1 × 1 | Melt extrusion |
| 12702-72-1 | 75/25 PLGA | 5 | mPEG | 1 × 1 | Melt extrusion |
| 12702-80-7 | 75/25 PLGA | 10 | mPEG | 0.75 × 0.75 | Melt extrusion |
| 12702-80-8 | 75/25 PLGA | 15 | mPEG | 0.75 × 0.75 | Melt extrusion |
| 13395-3-1 | 85/15 PLGA | 10 | mPEG | 0.75 × 0.75 | Melt extrusion |
| 13395-3-2 | 85/15 PLGA | 15 | mPEG | 0.75 × 0.75 | Melt extrusion |
| 13395-3-3 | 85/15 PLGA | 5 | mPEG | 0.75 × 0.75 | Melt extrusion |
| 13395-15 | 85/15 PLGA | 15 | mPEG | 0.75 × 0.75 | Melt extrusion |
| 13395-20-1 | 85/15 PLGA | 5 | Span-85 | 0.75 × 0.75 | Melt extrusion |
| 13395-20-2 | 85/15 PLGA | 5 | Pluronic-F127 | 0.75 × 0.75 | Melt extrusion |
| 13395-20-3 | 85/15 PLGA | 5 | N/A | 0.75 × 0.75 | Melt extrusion |
| 13395-21-1 | D,L-PLA | 5 | mPEG | 0.75 × 0.75 | Melt extrusion |
| 13395-21-2 | 85/15 PLGA | 5 | TBO-Ac | 0.75 × 0.75 | Melt extrusion |
| 13395-24-1 | 85/15 PLGA | 5 | Span-65 | 0.75 × 0.75 | Melt extrusion |
| 13395-27-1 | 85/15 PLGA | 10 | N/A | 0.75 × 0.75 | Melt extrusion |
| 13395-27-2 | 85/15 PLGA | 15 | N/A | 0.75 × 0.75 | Melt extrusion |
| 13395-27-3 | 85/15 PLGA | 10 | Span-65 | 0.75 × 0.75 | Melt extrusion |
| 13395-27-4 | 85/15 PLGA | 10 | TBO-Ac | 0.75 × 0.75 | Melt extrusion |
| 13395-27-5 | 85/15 PLGA | 10 | Pluronic F127 | 0.75 × 0.75 | Melt extrusion |
| 13395-34-2 | D,L-PLA | 10 | N/A | 0.75 × 0.75 | Melt extrusion |
| 13395-34-3 | D,L-PLA | 10 | TBO-Ac | 0.75 × 0.75 | Melt extrusion |
| 13395-34-4 | D,L-PLA | 10 | mPEG | 0.75 × 0.75 | Melt extrusion |
| 13395-42-1 | DL-PLA/PCL | 10 | N/A | 0.75 × 0.75 | Melt extrusion |
| 13395-42-2 | DL-PLA/PCL | 15 | N/A | 0.75 × 0.75 | Melt extrusion |

TABLE 2

| Notebook ID | Polymer Type | Drug Load (Wt. %) | Excipient | Pellet Size (L × Dia; mm) or Description | Processing |
|---|---|---|---|---|---|
| 13335-73-1 | POE 58 | 10 | N/A | 1.5 × 0.75 | Melt extrusion |
| 13335-73-2 | POE 58 | 20 | N/A | 0.75 × 0.75 | Melt extrusion |
| 13335-73-3 | POE 60 | 10 | N/A | 1.5 × 0.75 | Melt extrusion |
| 13335-73-4 | POE 60 | 20 | N/A | 0.75 × 0.75 | Melt extrusion |
| 13699-1-2 | POE 58 | 10 | N/A | 4-1.5 × 0.75 | Melt extrusion |
| 13699-1-3 | POE 58 | 20 | N/A | 1-0.75 × 0.75 | Melt extrusion |
| 12702-23 | tCHDM (100) | 25 | N/A | Microspheres | Double emulsion |
| 12702-26 | tCHDM/DET (70/30) | 4.2 | N/A | Microspheres | Double emulsion |
| 12702-54 | 75/25 PLGA | 20 | N/A | Microspheres | Double emulsion |
| 12702-68-9 | 75/25 PLGA | 5 | mPEG | 3 × 3 | Melt extrusion |
| 12702-68-10 | 75/25 PLGA | 5 | TBO-Ac | 3 × 3 | Melt extrusion |
| 12702-87 | 75/25 PLGA | 15 | mPEG | | Mixer-Molder |
| 12702-90 | 85/15 PLGA | 17 | N/A | | Mixer-Molder |
| 12702-78-1 | Polyketal (12833-14-1) | 7 | N/A | 2 × 3 | Melt extrusion |
| 13395-14 | 50/50 PLGA (2A) | 10 | mPEG | N/A | Melt extrusion |
| 13395-17-1 | POE (13166-75) | 5 | N/A | 1.5 × 1.5 | Melt extrusion |
| 13395-17-2 | POE (13166-77) | 5 | N/A | 1.5 × 1.5 | Melt extrusion |
| 13395-47-1 | DL-PCL | 10 | N/A | 1.3 × 1.3 | Melt extrusion |
| 13395-50 | DL-PCL | 10 | N/A | 1.3 × 1.3 | Melt extrusion; w/ solvent prep |
| 13395-51 | D,L-PLA | 10 | mPEG | N/A | Melt extrusion |

TABLE 3

| Notebook ID | Polymer Type | Drug Load (Wt. %) | Processing |
|---|---|---|---|
| 00178-23 | 100 DL 5E | 8.1 | Melt extrusion, hand mixed |
| 00178-15 | 100 DL 7E | 7.2 | Melt extrusion, hand mixed |
| 00178-35 | 100 DL 5E | 5 | Melt extrusion, hand mixed |
| 00178-16 | 100 DL 7E | 10.2 | Melt extrusion, hand mixed |
| 00178-21 | 8515 DL 7E | 7.3 | Melt extrusion, hand mixed |
| 00178-36 | 100 DL 7E | 5 | Melt extrusion, hand mixed |
| 00178-44 | 100 DL 7E | 5.1 | Dissolved in glacial acetic acid, freeze dried, melt extrusion |
| 00178-45 | 100 DL 7E | 4.5 | Drug and polymer blend, prepared in N2 environment, melt extrusion |
| 00178-45-C | 100 DL 7E | 4.5 | Formulation 00178-45 with EtOAc coating |
| 00178-63 | 100 DL 7E | 9.4 | Melt extrusion |
| 00178-08 | 100 DL 7E | 21.4 | melt extrusion, no reduction in drug particle size |
| 00178-11 | 100 DL 7E | 7.9 | melt extrusion, no reduction in drug particle size |
| 00178-12 | 100 DL 7E | 11.7 | melt extrusion, no reduction in drug particle size |
| 00178-22 | 8515 DL 7E | 8.3 | melt extrusion |
| 00178-24 | 100 DL 5E | 10.1 | melt extrusion |
| 00178-23-C | 100 DL 5E | 8.1 | Formulation 00178-23 with EtOAc coating |
| 00178-23-PC | 100 DL 5E | 8.1 | Formulation 00178-23 with polymer solution coating |
| 00178-35-C | 100 DL 5E | 5 | Formulation 00178-35 with EtOAc coating |
| 00178-36-C | 100 DL 7E | 5 | Formulation 00178-36 with EtOAc coating |
| 00178-72 | 100 DL 7E | 4.5 | Double Extrusion (20% diluted to 5%) |
| 00178-73 | 100 DL 7E | 8.7 | Double Extrusion (20% diluted to 10%) |
| 00178-74 | 6353 DLG 7E | 7.3 | Melt extrusion, hand mixed |
| 00178-71 | 6535 DLG 7E | 5.3 | Melt extrusion, hand mixed |
| 00178-75 | 6535 DLG 7E | 3.3 | Melt extrusion, hand mixed |
| 00178-76-R1 | 100 DL 7E core with 100DL 5E coating | 7.76 | coaxial extrusion, 4 different coating thicknesses |
| 00178-76-R2 | 100 DL 7E core with 100DL 5E coating | 6.92 | coaxial extrusion, 4 different coating thicknesses |
| 00178-76-R3 | 100 DL 7E core with 100DL 5E coating | 6.76 | coaxial extrusion, 4 different coating thicknesses |
| 00178-76-R4 | 100 DL 7E core with 100DL 5E coating | 8 | coaxial extrusion, 4 different coating thicknesses |
| 00178-79-R1 | 100 DL 5E core with 100DL 5E coating | 12.1 | coaxial extrusion, thin coat |
| 00178-80-R1 | 100 DL 5E core with 100DL 5E coating | 7.54 | coaxial extrusion, different coating thicknesses |
| 00178-80-R3 | 100 DL 5E core with 100DL 5E coating | 8.9 | coaxial extrusion, different coating thicknesses |
| 00178-80-R4 | 100 DL 5E core with 100DL 5E coating | 10.0 | coaxial extrusion, different coating thicknesses |

TABLE 3-continued

| Notebook ID | Polymer Type | Drug Load (Wt. %) | Processing |
|---|---|---|---|
| 00178-77 | 100 DL 5E | 5.2 | repeat of 178-35 (1.0 mm diameter) |
| 00178-78 | 100 DL 5E | 5.1 | repeat of 178-35 (0.8 mm diameter) |
| 00178-81 | 100 DL 5E | 7.2 | repeat of 178-23 |
| 00178-87 | 100 DL 5E | 5.0 | Repeat of 178-35 (1.0 mm diam) |
| 00178-90 | 100 DL 5E | 5 | Repeat 178-35, mechanical mixing, single screw melt extrusion (0.8 mm and 1.0 mm diameter) |
| 00178-91-R1 | 100 DL 5E core with 100 DL 5E coating | 3.5 | Coaxial extrusion, thick coating |
| 00178-91-R6 | 100DL 5E core with 100 DL 5E coating | 7.4 | Coaxial extrusion, thin coating |
| 00178-93-R3 | 100 DL 5E core with 100 DL 7E coating | 5 | Coaxial extrusion, mechanical mixing, thin coating layer |
| 00178-93-R4 | 100 DL 5E core with 100 DL 7E coating | 3.8 | Coaxial extrusion, mechanical mixing, thick coating layer |

The codes within the table for the polymer are explained as follows. The first number or numbers refer to the monomer mole percentage ratio of DL-lactide (e.g., polylactide) to glycolide (e.g., poly-glycolide). The letter code that follows the first number refers to the polymer(s) and is the polymer identifier. The second number, which follows the letter code for the polymer, is the target IV designator and is 10 times the midpoint of a range in dl/g. The meanings of certain IV designators are reflected in Table 4.

TABLE 4

| IV Target Designator | IV Range |
|---|---|
| 1 | 0.05-0.15 |
| 1.5 | 0.10-0.20 |
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |
| 8 | 0.70-0.90 |
| 9 | 0.80-1.0 |

The final letter within the code of the polymer is the end group designator. For example, "E" refers to an ester end group, while "A" refers to an acid end group.

By way of example, 100 DL7E is a polymer that has an inherent viscosity of 0.60-0.80 dL/g. It contains 100% poly (DL-lactide) that has ester end groups. It is available from Lakeshore Biomaterials, Birmingham, Ala.

Figure 7:
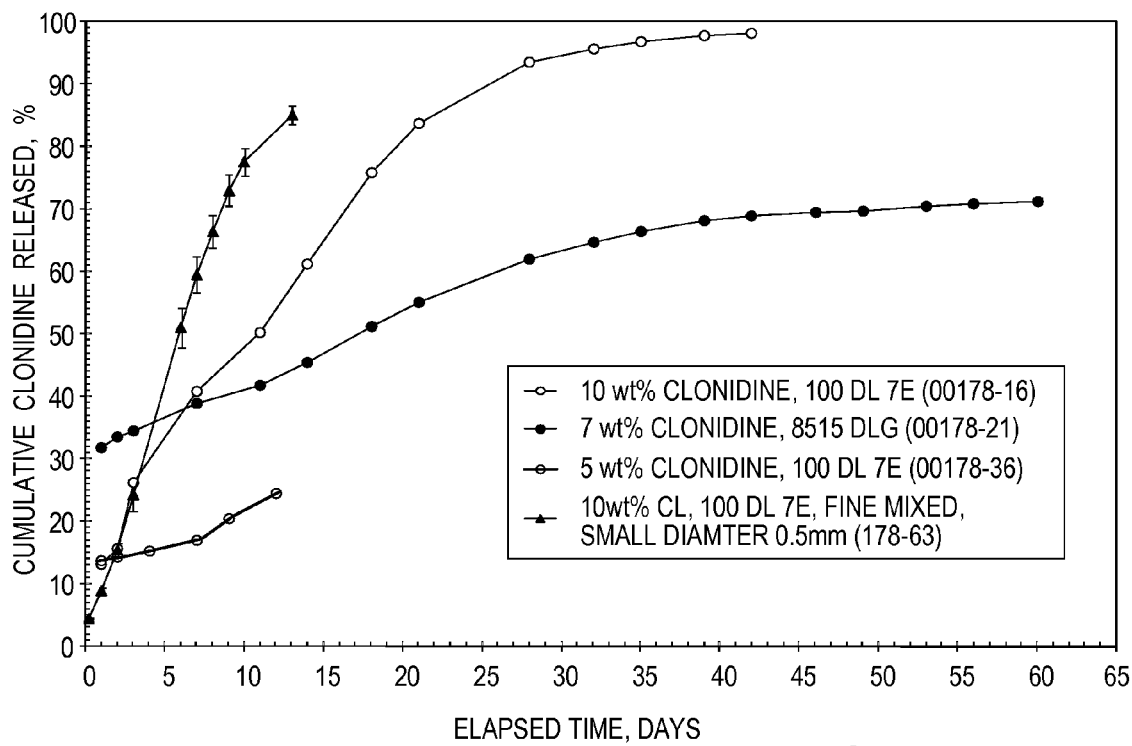
FIG. 7 is a graphic representation of clonidine HCl release for various formulations as measured by the cumulative clonidine released percentage.

FIG. 7 is a graphic representation of clonidine HCl release for various formulations (identified in Table 3) as measured by the cumulative clonidine released percentage. In FIG. 7, the formulations contained: 10 wt. % clonidine, the remainder 100 DL 7E (the inherent viscosity of the 100 DL was 0.60-0.80 and had an ester end group) or 7 wt. % clonidine, the remainder 8515 DLG or 5 wt. % clonidine, the remainder 100 DL 7E (the inherent viscosity of the 100 DL was 0.60-0.80 and had an ester end group), or 10 wt. % clonidine, the remainder 100 DL 7E (the inherent viscosity of the 100 DL was 0.60-0.80 and had an ester end group) and the pellets had small diameters of 0.5 mm. The clonidine formulation with the 10% drug load had a faster release also because it had a smaller diameter, but increased surface area, which allowed a faster drug release. This formulation was dispersed better in the polymer as indicated by the fine mixing legend. The 10% clonidine formulation that was thicker in diameter and was less dispersed throughout the polymer had a slower release profile. The lower drug load formulation of 7% had the longest release period of over 60 days. In general, increasing the drug load was found to cause a more rapid release of the drug while the lower drug loads were found to produce a more sustained release effect. All formulations had an initial burst release within 1-2 days of between 5% and 35% cumulative clonidine release.

Figure 8:
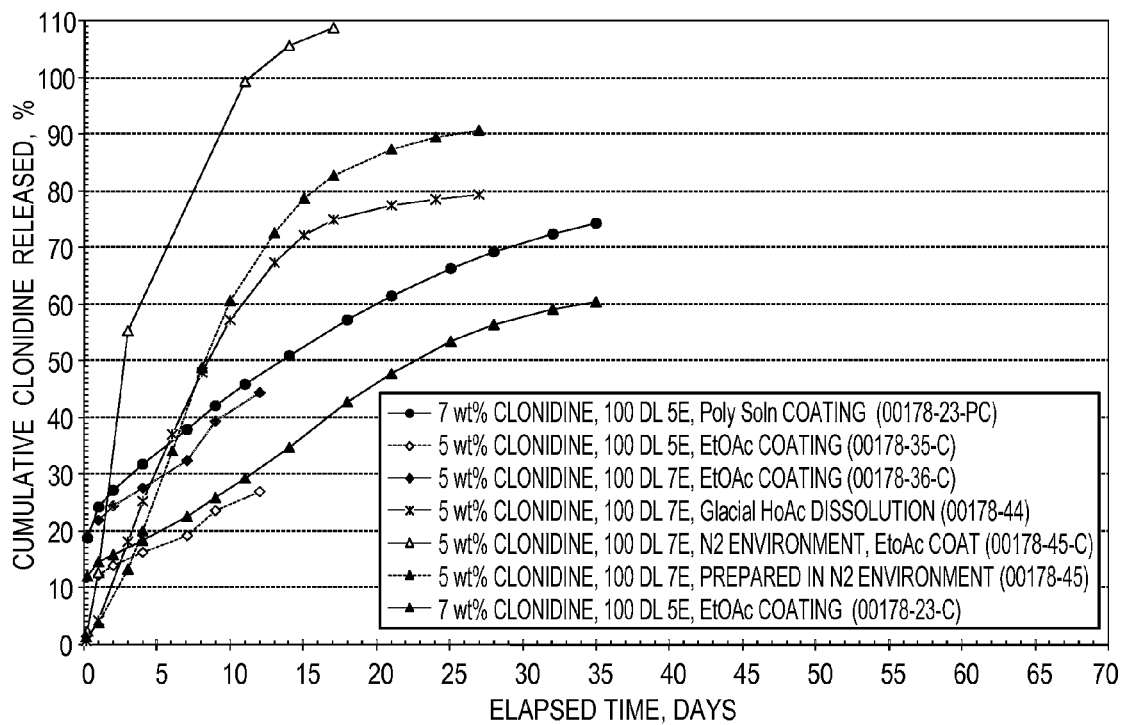
FIG. 8 is a graphic representation of the cumulative in vitro release profile for certain clonidine formulations.

FIG. 8 is a graphic representation of the cumulative in vitro release profile for certain clonidine formulations having different processing. The depots had PLG polymer coatings (poly soln), solvent coating with ethyl acetate (EtOAC), glacial acetic acid (glacial HoAc), or was processed in a nitrogen environment and coated with ethyl acetate as indicated in the legend. The coatings can be applied by methods known in the art (e.g., spray coating, dip coating, etc.). The solvents used to coat the depot can be solvents known in the art, for example, acetone, methyl chloride, chloroform, EtOAC, etc. The coatings produced a release from 12 to 35 days with the fastest release (over 100%) in the formulation that was placed in a nitrogen environment. The longest release was observed for the formulation with the polymer coating and high drug load of clonidine 7 wt. % where drug was released for over 35 days.

Figure 9:
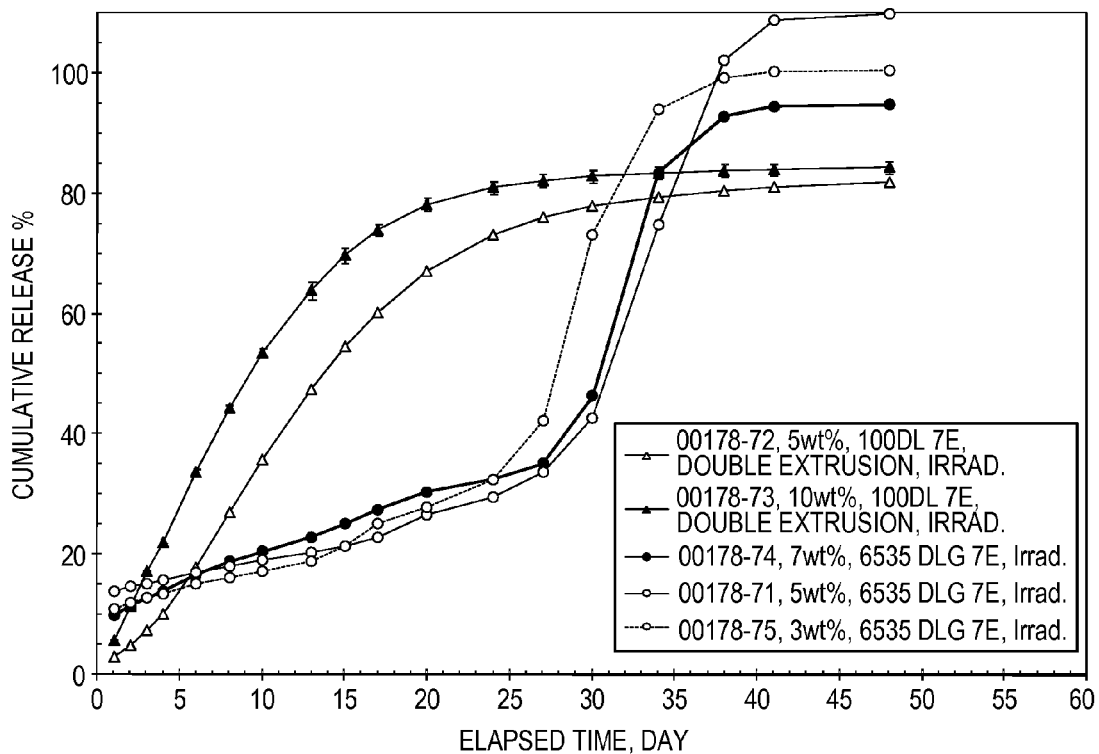
FIG. 9 is a graphic representation of the cumulative release profiles for certain irradiated clonidine HCl formulations.

FIG. 9 is a graphic representation of the cumulative release profiles for certain irradiated clonidine HCl formulations produced as indicated in Table 3. The slowest release was seen for clonidine formulations that were double extruded, where a first batch was mixed and then extruded and then that batch was mixed again and extruded to form the double extruded composition. These formulations had a slower polymer degradation and drug release at about day 30 when compared to formulations that were not double extruded. The formulations with the DLG 7E (the inherent viscosity of the 100 DL was 0.60-0.80 and had an ester end group) polymer had a rapid release and a second burst about day 30.

Figure 10:
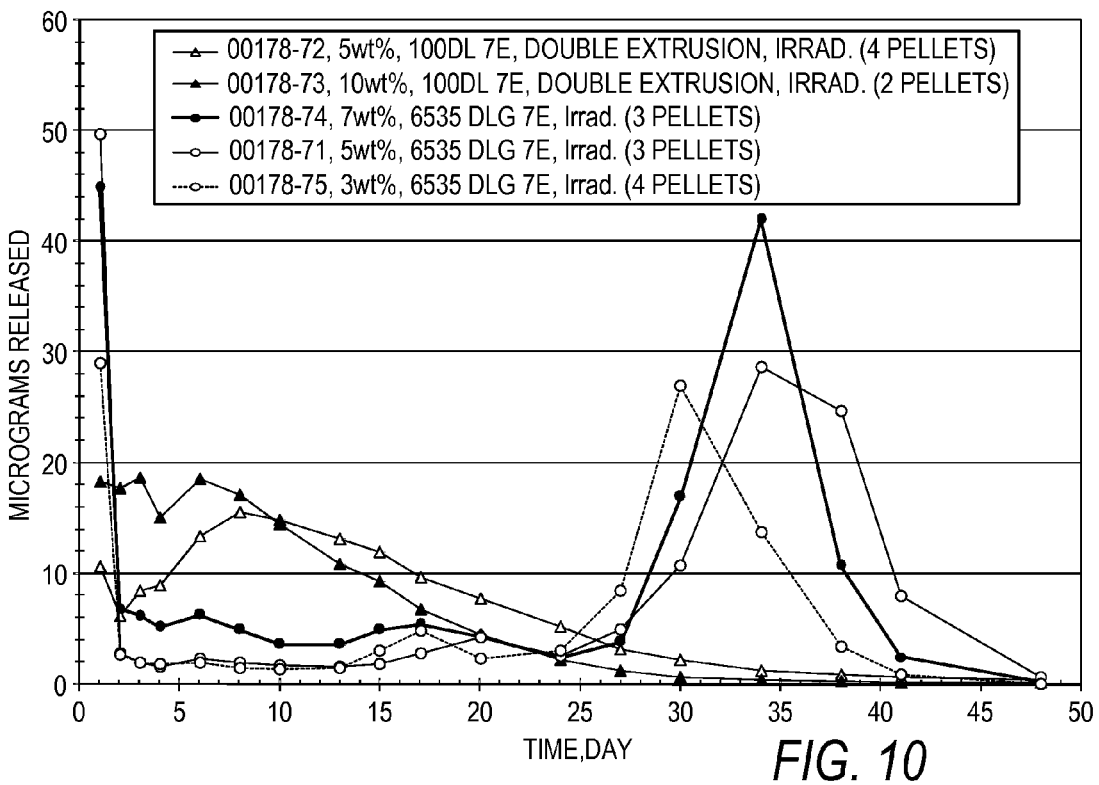
FIG. 10 is a graphic representation of certain calculated daily release measurements of clonidine from 2/3/4 pellets doses.

FIG. 10 is a graphic representation of certain calculated daily release measurements of clonidine from 2/3/4 pellet doses. The slowest release was seen for clonidine formulations that were double extruded, where a first batch was mixed and then extruded and then that batch was mixed again and extruded to form the double extruded depot. These formulations had a slower polymer degradation and drug release at about day 30, when compared to formulations that were not double extruded. The formulations with the DLG 7E (the inherent viscosity of the 100 DL was 0.60-0.80 and had an ester end group) polymer had a rapid release and a second burst about day 30. All formulations had an initial burst release on day one from about 10 mcg-50 mcg and the daily release ranged from 0.5 mcg to 20 mcg/day over about 48 days. The formulations that were not double extruded had a second initial burst at around day 25 to day 35 as indicated by the large peaks. These formulations did not have polymer coatings on the depot and, thus, had high initial bursts ranging from 30 mcg-50 mcg.

Figure 11:
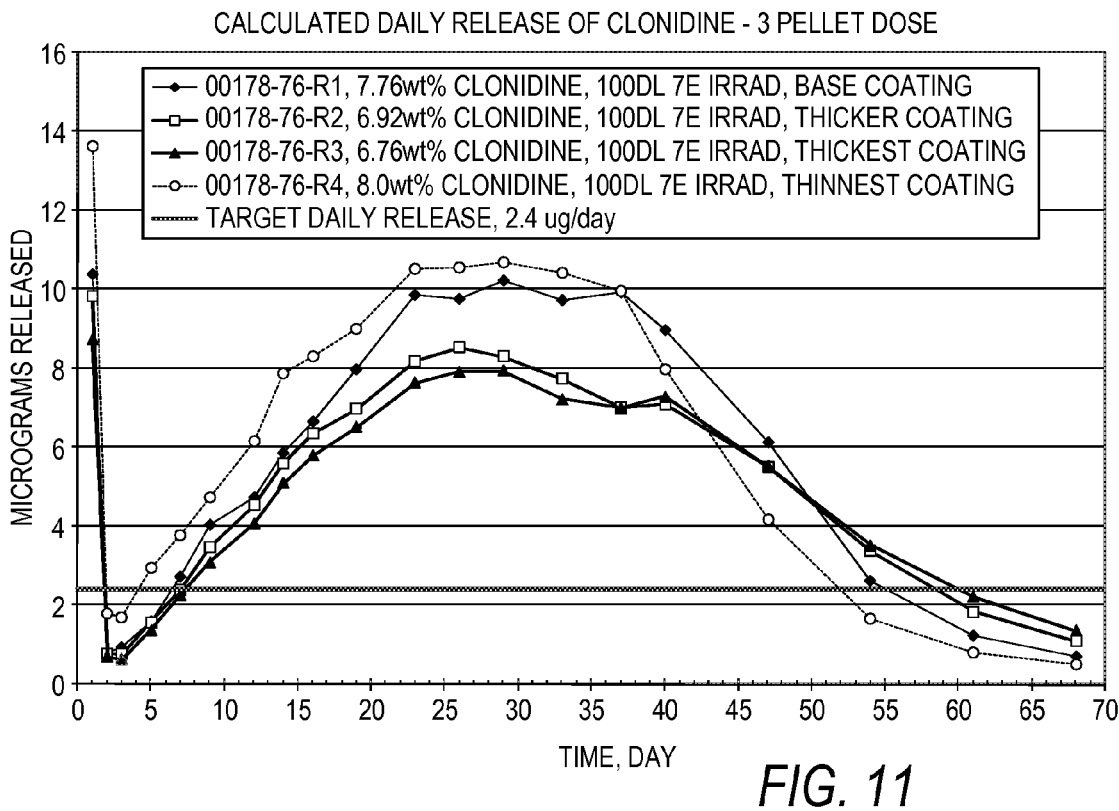
FIG. 11 is a graphic representation of the calculated daily release of clonidine from certain three pellet doses.

FIG. 11 is a graphic representation of the calculated daily release of clonidine from certain three pellet doses produced as indicated in Table 3. Each pellet (drug depot) had an inner core of drug and polymer and an outer coating with varying degrees of thickness (a thick coating is about 50~100 microns and a thin coating is about 5 microns to about ~20 microns). The thinnest coating (about 20 microns) had the highest initial burst ranging from about 9-14 mcg, which was much less than the uncoated depots from FIG. 10. The formulations in FIG. 11 were designed to decrease the initial burst with the outer coating. In general, the thicker the coating on the polymer drug core, the slower the drug release from the depot.

Figure 12:
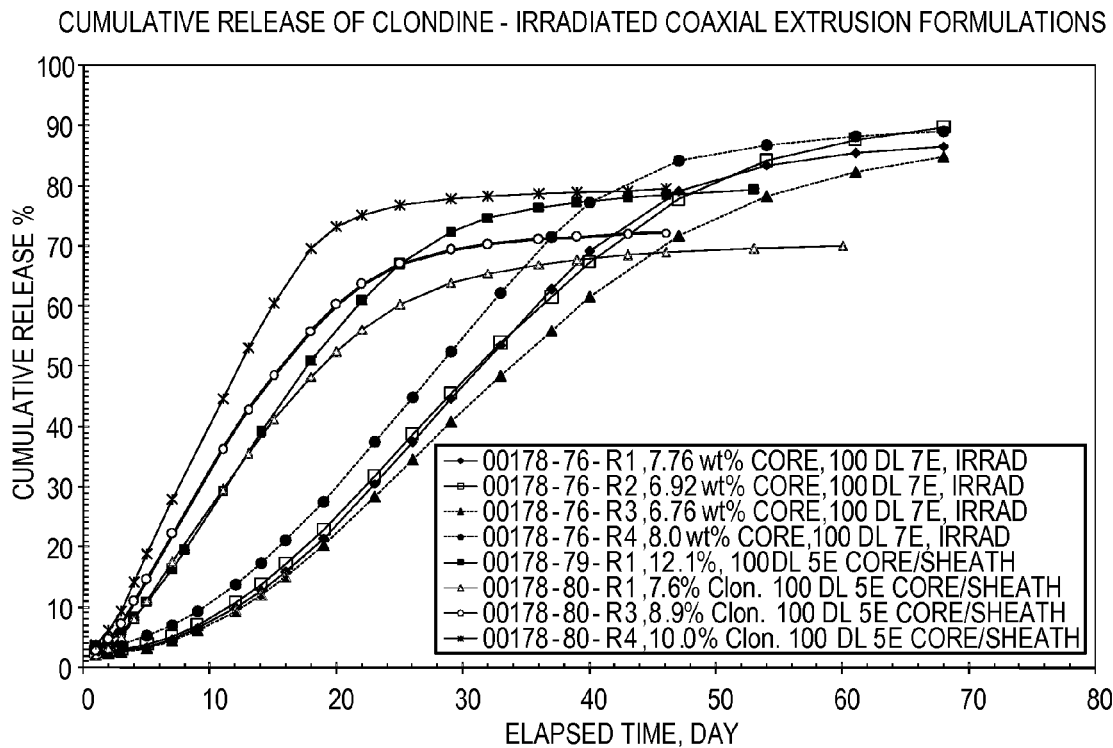
FIG. 12 is a graphic representation of the cumulative in vitro release profile of clonidine from certain coaxial formulations.

FIG. 12 is a graphic representation of the cumulative in vitro release profile of clonidine from certain coaxial formulations (Table 3). The formulations containing clonidine loads having 7.76 wt. %, 6.92 wt. %, 6.76 wt. %, or 8.0 wt. % had a polymer and drug core with no outer coating. In general, with respect to these 4 formulations, the higher the drug loads, the faster the drug release and more release of the drug from the depot. For example, the drug depot having an 8.0 wt. % drug load (the highest load in the core group) released about 90 wt. % of the drug from the depot at about 70 days. In the second group, the formulations containing clonidine loads having 12.1 wt. %, 7.6 wt. %, 8.9 wt. % or 10.0 wt. % had a polymer and drug core with an outer coating to delay release. The higher the drug load, the thinner the coating and the lower the drug load, the thicker the coating. These results show that by varying the drug load, changing the polymer from DL 7E (the inherent viscosity of the 100 DL was 0.60-0.80 and had an ester end group) to DL 5E (the inherent viscosity of the 100 DL was 0.45-0.55 and had an ester end group) and changing the coating thickness (a thick coating is about 50~100 microns and a thin coating would be 5 to about ~20 microns), the release profile of the drug depot was changed wherein the higher drug loads (12.1 wt. % and 10 wt. %) had a higher % cumulative release and the lower drug loads (8.9 wt. % and 7.6 wt. %) had a lower % cumulative release.

Figure 13:
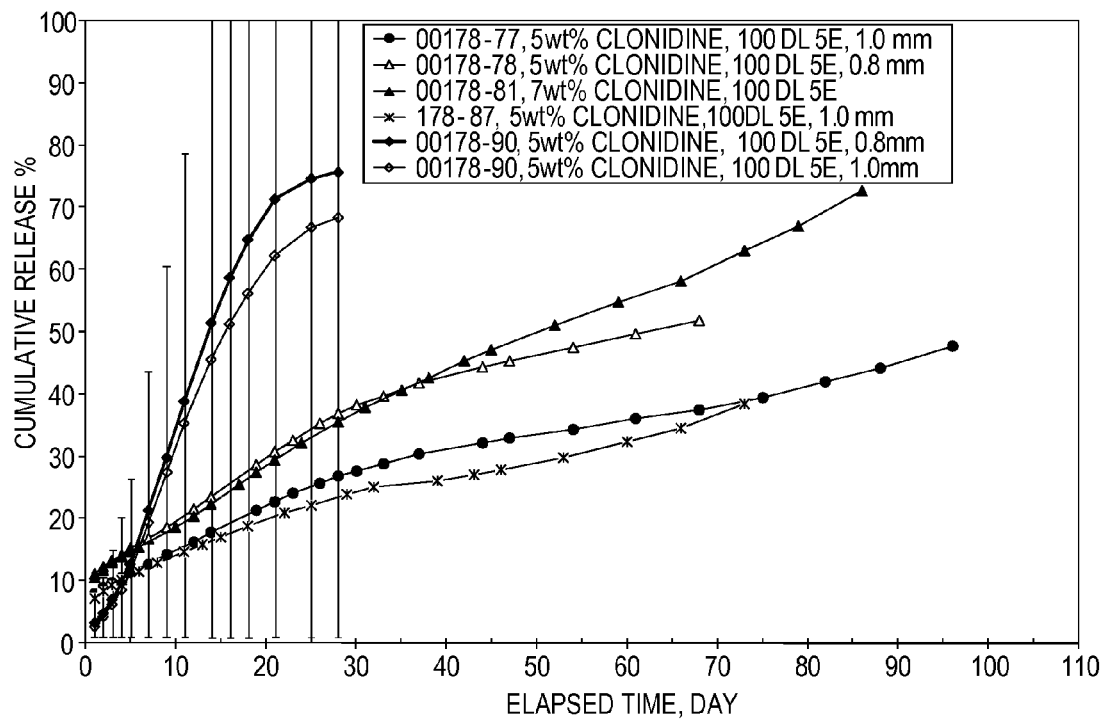
FIG. 13 is a graphic representation of the cumulative in vitro release profile for certain irradiated clonidine formulations.

FIG. 13 is a graphic representation of the cumulative in vitro release profile for certain irradiated clonidine formulations in Table 3. The formulations contained 5 wt. % clonidine drug loads and the drug depot was either 1 mm or 0.8 mm. One formulation had a drug load of 7 wt. %. None of the formulations had a polymer coating. In general, the smaller the diameter of the pellet, the more rapid release of the drug from the drug depot as the smaller diameter pellets had increased surface area which can lead to a higher % cumulative release of drug from the drug depot.

Figure 14:
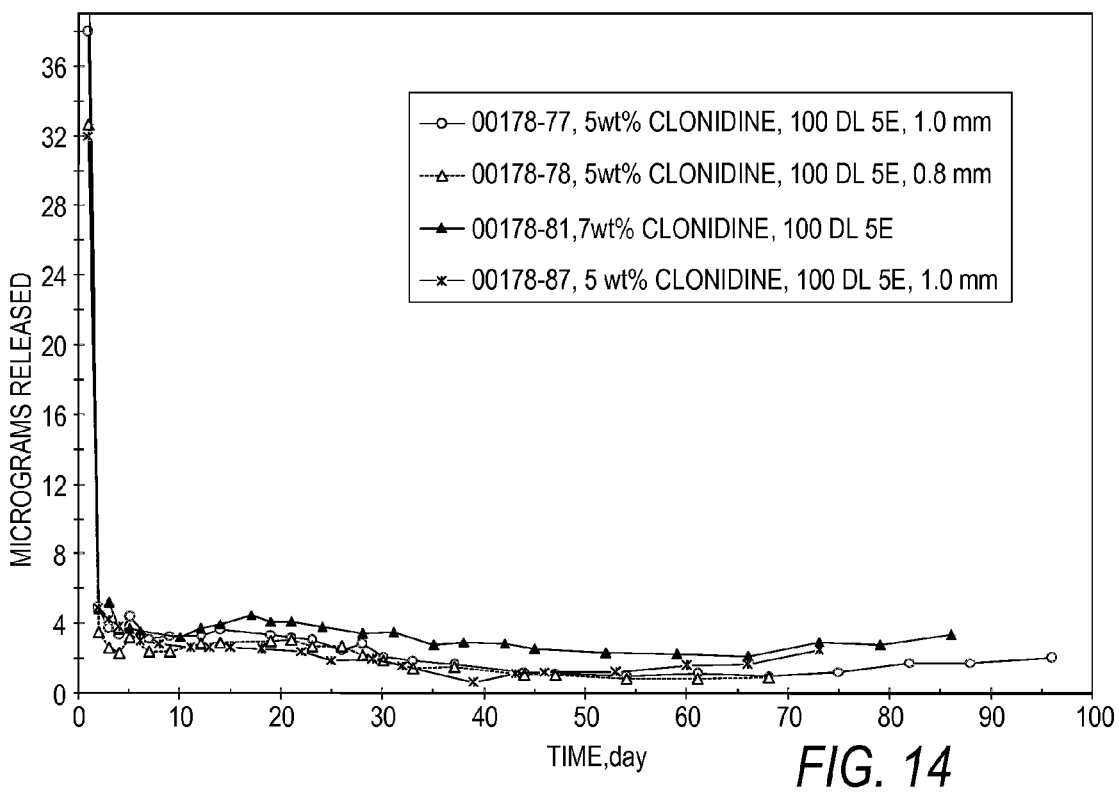
FIG. 14 is a graphic representation of the calculated daily release of clonidine for certain three pellet dose formulations.

FIG. 14 is a graphic representation of the calculated daily release of clonidine for certain three pellet dose formulations of FIG. 13 that did not have coatings on them. All formulations had a high initial burst release on day one from about 28 mcg-32 mcg and daily release ranged from 0.5 mcg to 4 mcg/day over about 75-95 days. There was no coating on these pellets, which lead to a high initial burst. All formulations had consistent release after the initial burst period.

Figure 15:
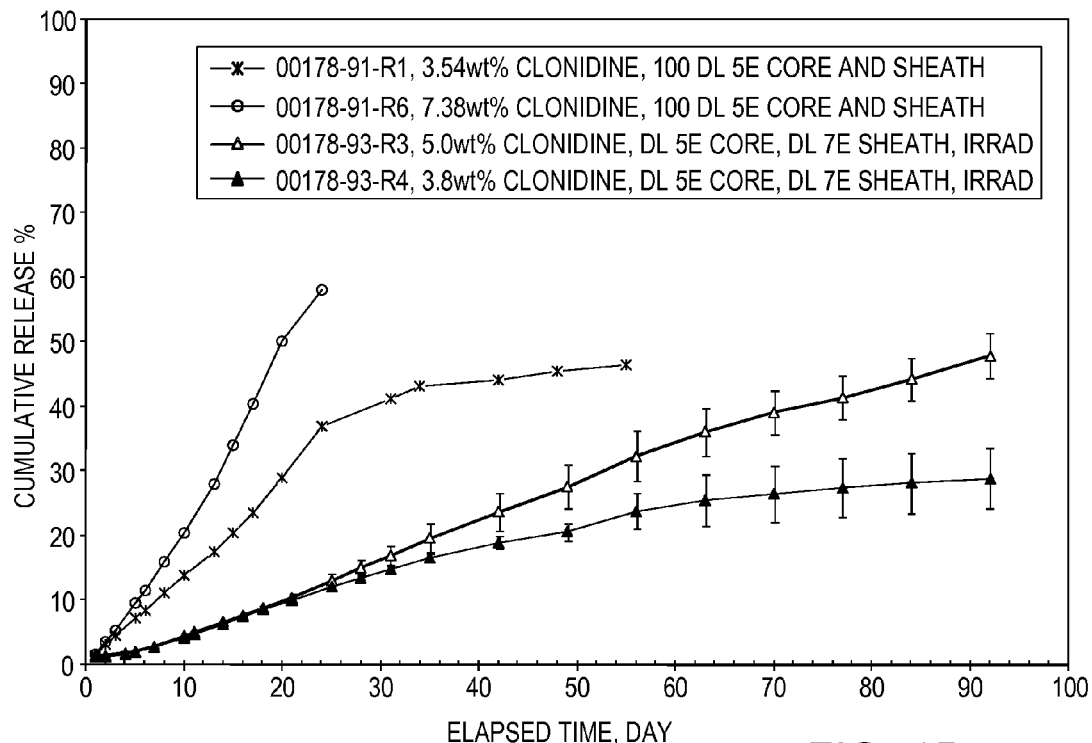
FIG. 15 is a graphic representation of the cumulative release percentage of clonidine for certain formulations.

FIG. 15 is a graphic representation of the cumulative release percentage of clonidine for certain formulations. The formulations containing clonidine loads having 3.54 wt. %, 7.38 wt. %, 5.0 wt. %, or 3.8 wt. % had polymer and drug core and polymer DL coating. The polymer for the drug core was 100 DL 5E (the inherent viscosity of the 100 DL was 0.45-0.55 and had an ester end group) and some had this polymer for the coating (sheath) as indicated in the legend. Others had the drug core polymer as DL 5E (the inherent viscosity of the DL was 0.45-0.55 and had an ester end group) and the polymer coating (sheath) on the core as indicated in the legend was DL 7E (the inherent viscosity of the DL was 0.60-0.80 and had an ester end group). The thinnest coating and highest drug load (7.38 wt. % clonidine) had the fastest release and thicker coating and lowest drug load (3.54 wt. % clonidine) had the slower drug release considering both groups had the same polymer and coating 100 DL 5E (a thick coating is about 50~100 microns and a thin coating would be 5 to about ~20 microns). The other group having 5.0 wt. % clonidine load and 3.8 wt. % clonidine load had a polymer core of DL 5E and a polymer coating of DL 7E (sheath), which delayed drug release. The drug depot with the higher drug load released the fastest. In general, the higher the drug loads, the faster the drug release and more release of the drug from the depot, also the thicker the coating the slower the drug release.

Figure 16:
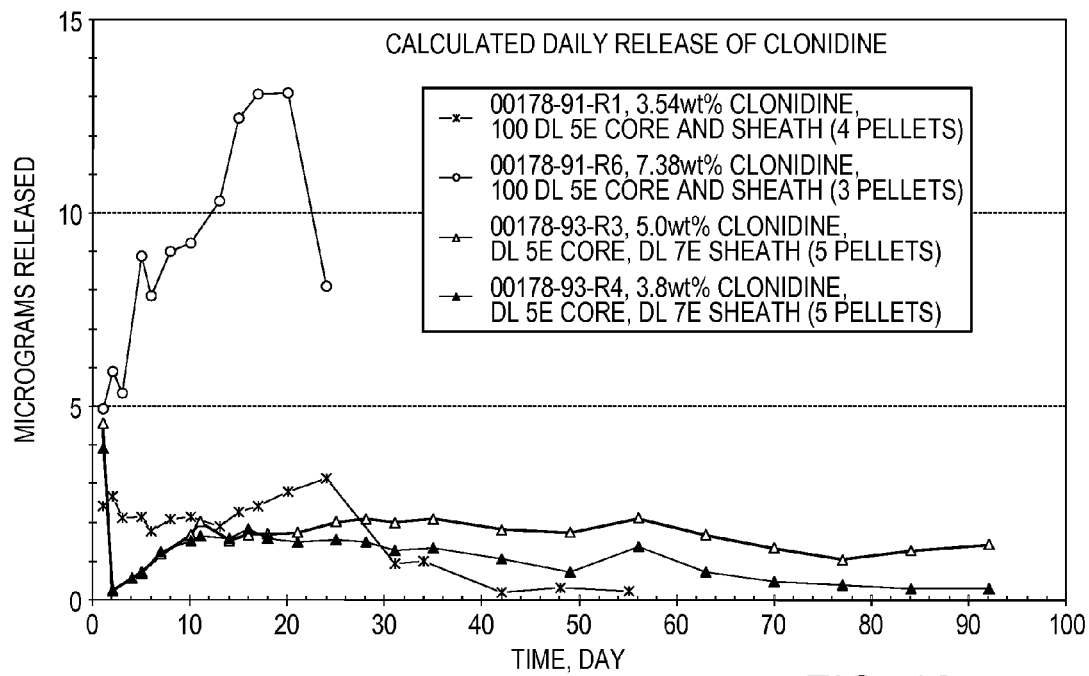
FIG. 16 is a graphic representation of the micrograms of clonidine released for certain 3/4/5 pellet dose formulations.

FIG. 16 is a graphic representation of the micrograms of clonidine released for certain 3/4/5 pellet dose formulations of FIG. 15. All formulations had either a 100 DL 5E coating on the core or a DL 7E coating on the core. All formulations had a lower initial burst effect as compared to uncoated pellets on day one, which was from about 3 mcg-5 mcg and daily release ranged from 0.1 mcg to 5 mcg/day over about 55-92 days. However, there was one formulation that had a high drug load of 7.38 wt. % clonidine that had the fastest release over about 25 days and a peak release of about 13 mcg. This formulation may be useful where a fast release is needed. All other formulations had consistent release after the initial burst period with some having a release over 90 days with a release of from about 0.1 mcg/day to about 3 mcg/day.

Figure 17:
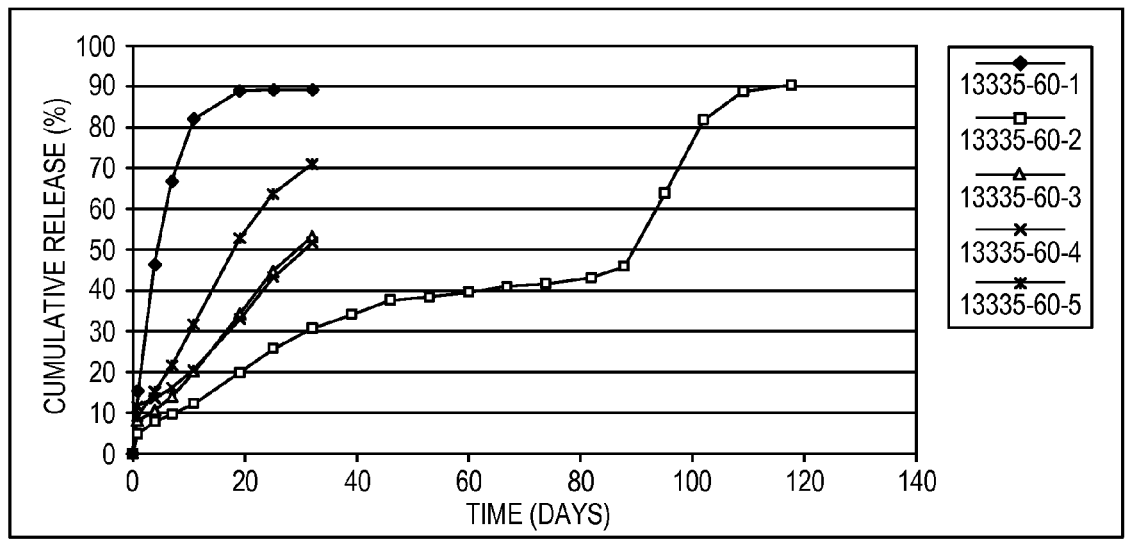
FIG. 17 is a graphic representation of the cumulative release percentage of clonidine for certain formulations.

FIG. 17 is a graphic representation of the cumulative release percentage of clonidine for certain formulations produced as indicated in Table 1. The formulation containing 10 wt. % clonidine drug load and the polymer 8515 DLG 7E had about 90 cumulative release % of drug released from the depot as long as 120 days, which is suitable for many chronic conditions.

Figure 18:
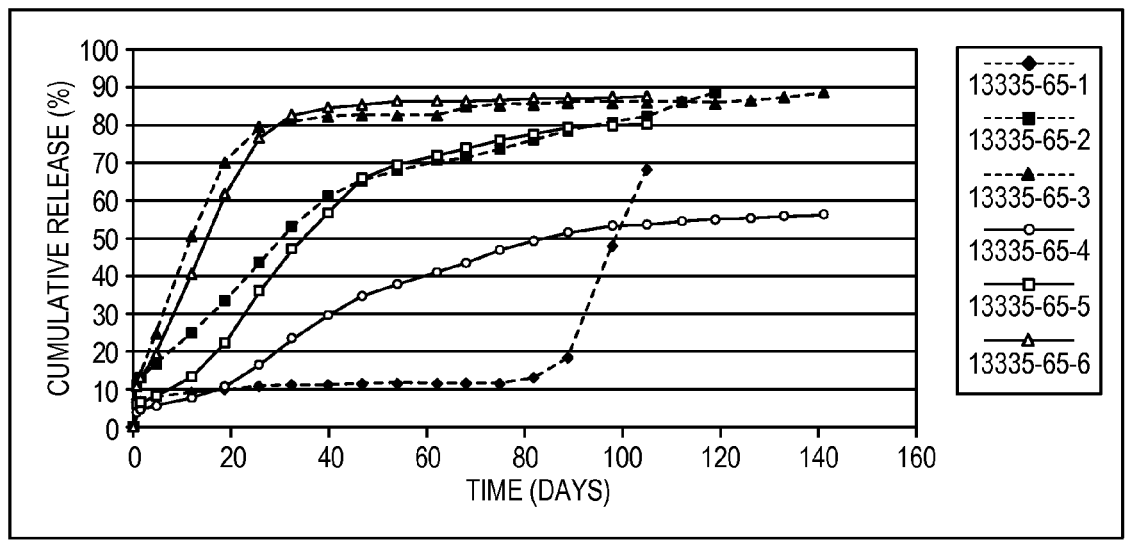
FIG. 18 is a graphic representation of the cumulative release percentage of clonidine for certain formulations.

FIG. 18 is a graphic representation of the cumulative release percentage of clonidine for certain formulations produced as indicated in Table 1. The formulation containing 20 wt. % clonidine drug load and the polymer 8515 DLG 7E had about 90 cumulative release % of drug released from the depot as long as 140 days, which is suitable for many chronic conditions.

Figure 19:
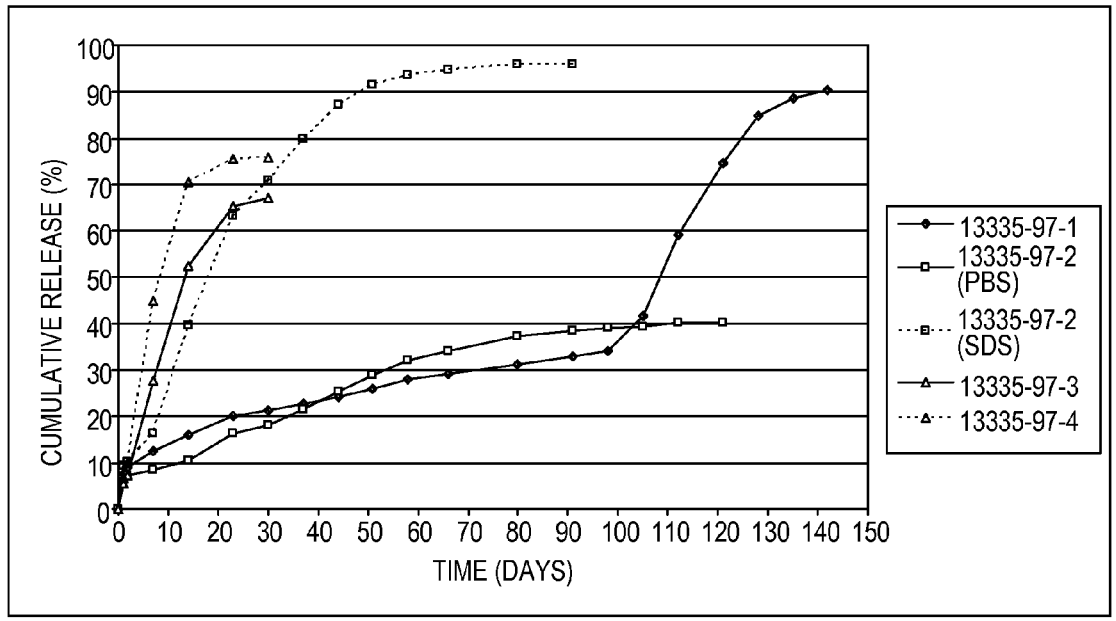
FIG. 19 is a graphic representation of the cumulative release percentage of clonidine for certain formulations.

FIG. 19 is a graphic representation of the cumulative release percentage of clonidine for certain formulations produced as indicated in Table 1. The formulation containing 7.5 wt. % clonidine drug load and the polymer 8515 DLG 7E had about 90 cumulative release % of drug released from the depot as long as 145 days, which is suitable for many chronic conditions.

Figure 20:
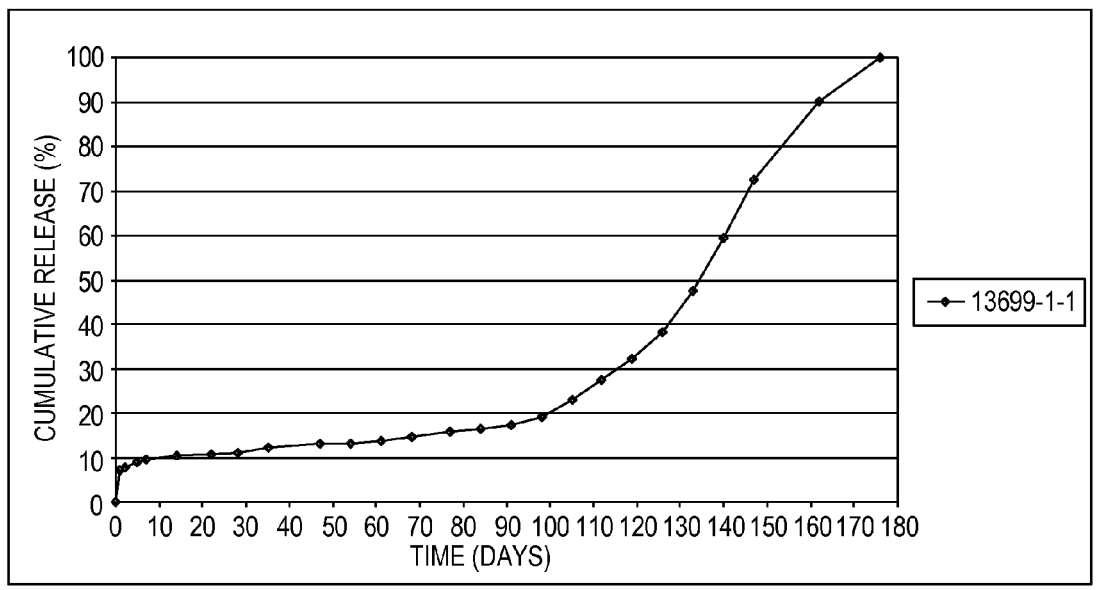
FIG. 20 is a graphic representation of the cumulative release percentage of clonidine for one formulation.

FIG. 20 is a graphic representation of the cumulative release percentage of clonidine for one formulation produced as indicated in Table 1. The formulation containing 5 wt. % clonidine drug load and the polymer 100 DL 7E had about 100 cumulative release % of drug released from the depot as long as 175 days, which is suitable for many chronic conditions.

Figure 21:
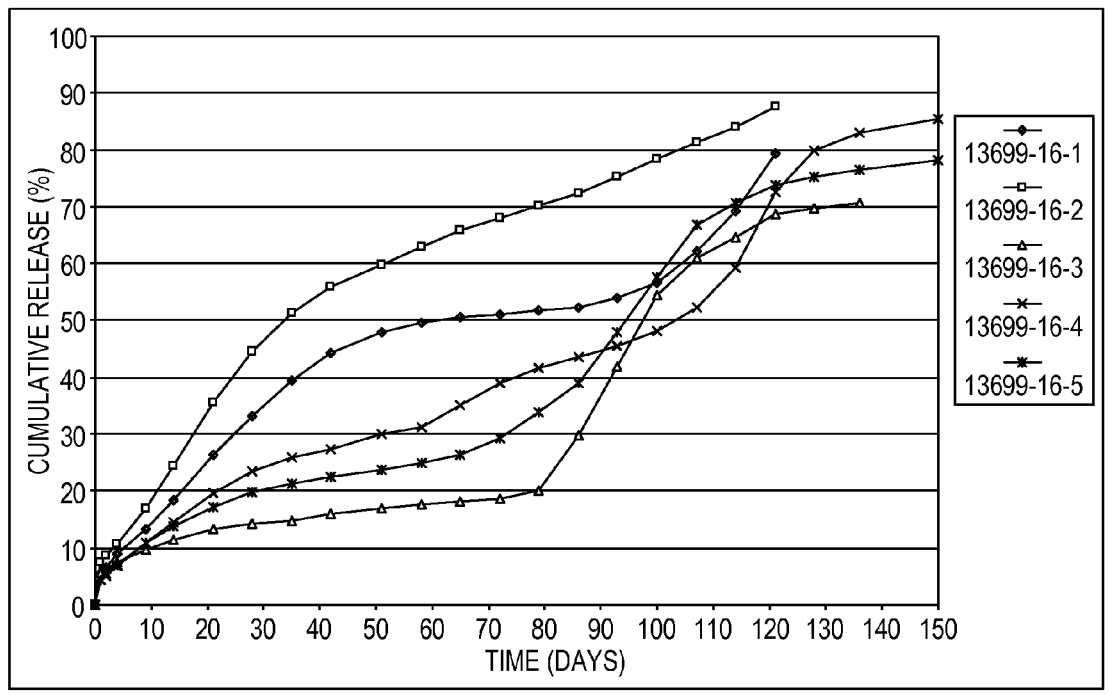
FIG. 21 is a graphic representation of the cumulative release percentage of clonidine for certain formulations.

FIG. 21 is a graphic representation of the cumulative release percentage of clonidine for certain formulations produced as indicated in Table 1. The formulation containing 5 wt. % clonidine drug load, the polymer 8515 DLG 7E and mPEG as a plasticizer had about 80 cumulative release % of drug released from the depot as long as 150 days, which is suitable for many chronic conditions.

Figure 22:
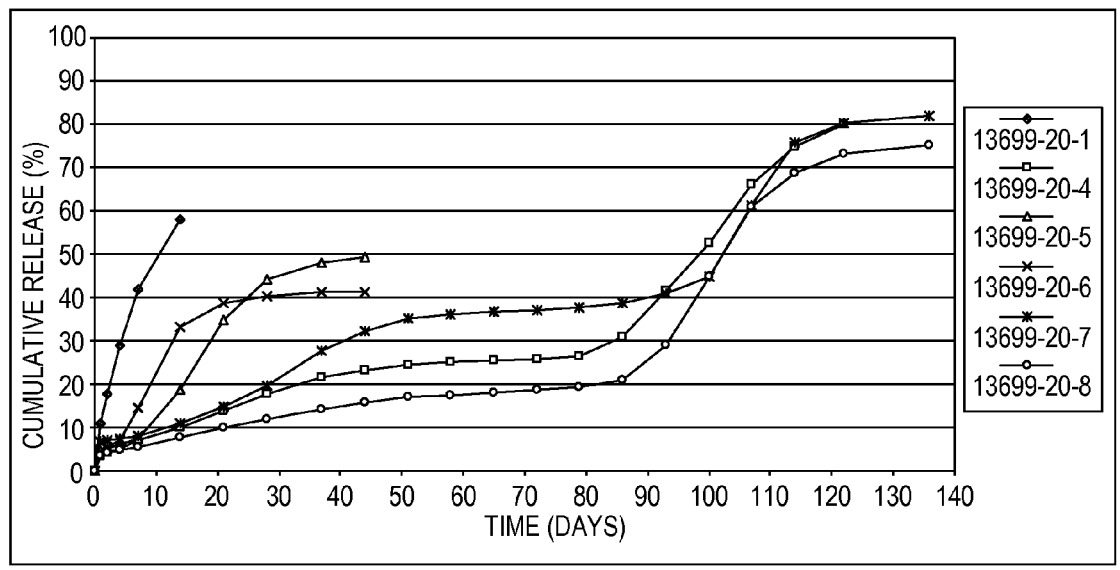
FIG. 22 is a graphic representation of the cumulative release percentage of clonidine for certain formulations.

FIG. 22 is a graphic representation of the cumulative release percentage of clonidine for certain formulations produced as indicated in Table 1. The formulation containing 5 wt. % clonidine drug load and the polymer 8515 DLG 7E had about 75 cumulative release % of drug released from the depot as long as 135 days, which is suitable for many chronic conditions.

Figure 23:
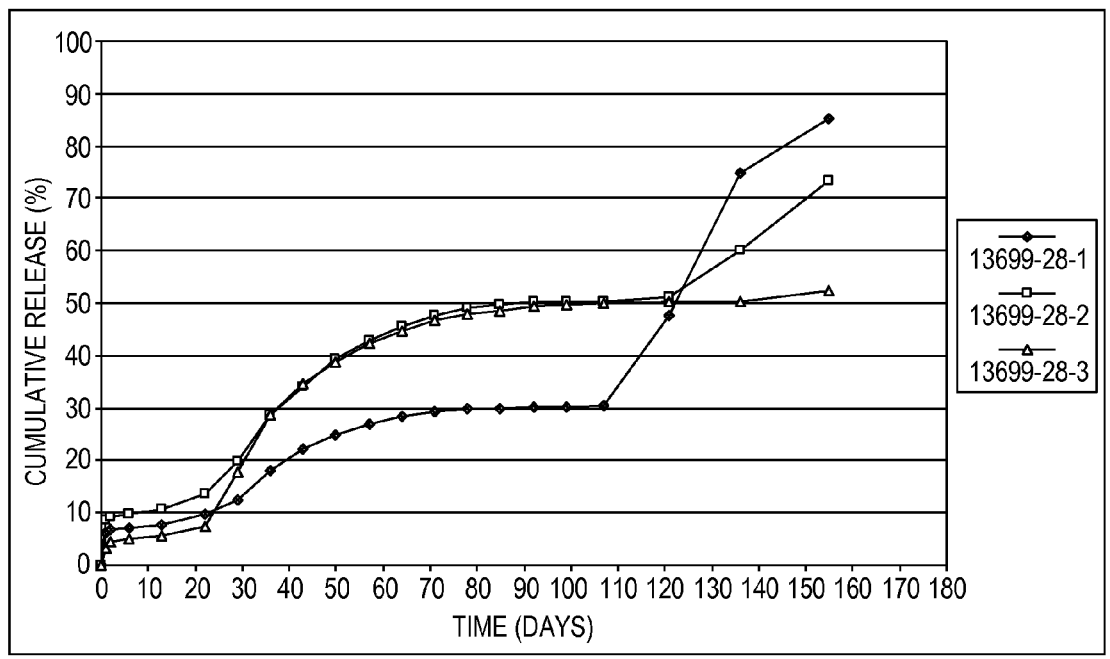
FIG. 23 is a graphic representation of the cumulative release percentage of clonidine for certain formulations.

FIG. 23 is a graphic representation of the cumulative release percentage of clonidine for certain formulations produced as indicated in Table 1. All formulations had about 50 to 75 cumulative release % of drug released from the depot as long as 160 days, which is suitable for many chronic conditions.

Figure 24:
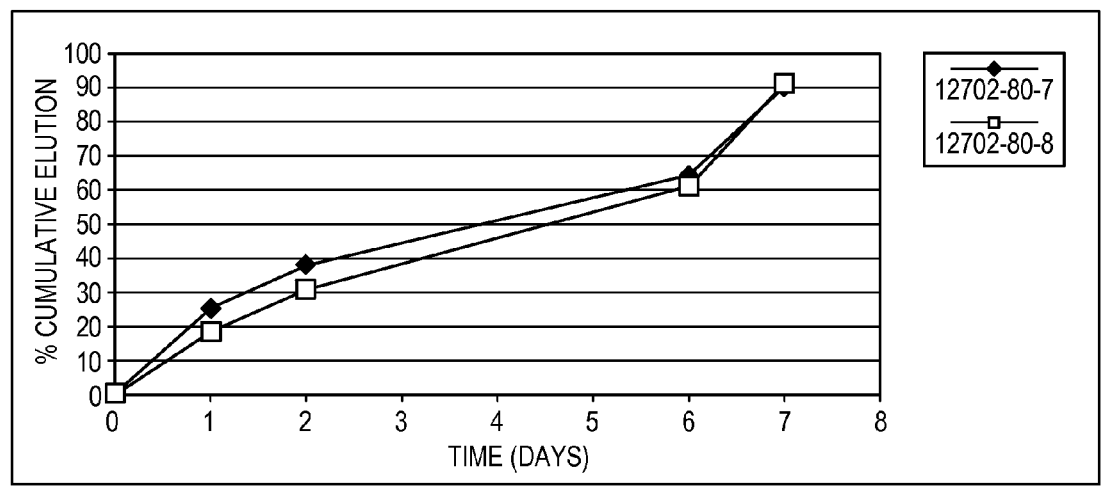
FIG. 24 is a graphic representation of the cumulative elution percentage of clonidine for certain formulations.

FIG. 24 is a graphic representation of the cumulative elution percentage of clonidine for certain formulations produced as indicated in Table 1. All formulations had about 90 cumulative release % of drug released from the depot for 7 days. The formulations were of a smaller size (0.75 mm×0.75 mm), which increases the surface area for release as compared to depots with larger diameters.

Figure 25:
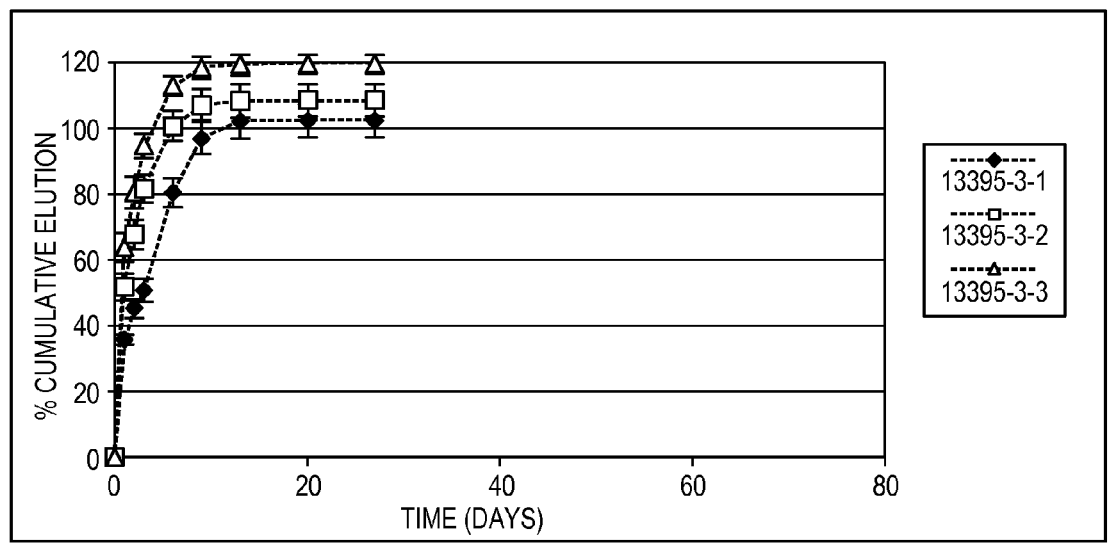
FIG. 25 is a graphic representation of the cumulative elution percentage of clonidine for certain formulations.

FIG. 25 is a graphic representation of the cumulative elution percentage of clonidine for certain formulations produced as indicated in Table 1. All formulations had over 100 cumulative release % of drug released from the depot for over 30 days.

Figure 26:
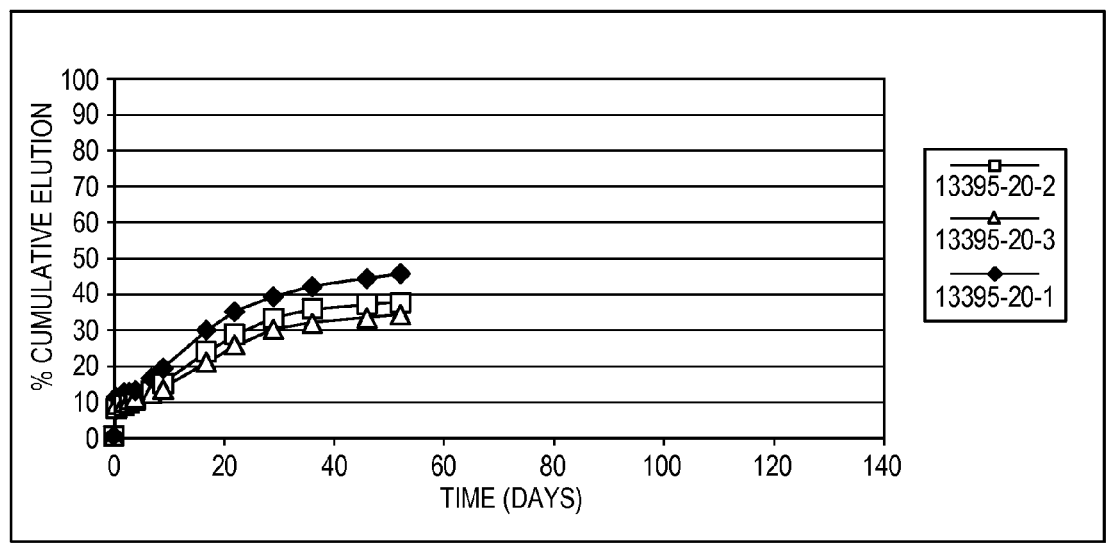
FIG. 26 is a graphic representation of the cumulative elution percentage of clonidine for certain formulations.

FIG. 26 is a graphic representation of the cumulative elution percentage of clonidine for certain formulations produced as indicated in Table 1. Span 85 is a plasticizer for one formulation. All formulations had about 30 to 50 cumulative release % of drug released from the depot for over 50 days.

Figure 27:
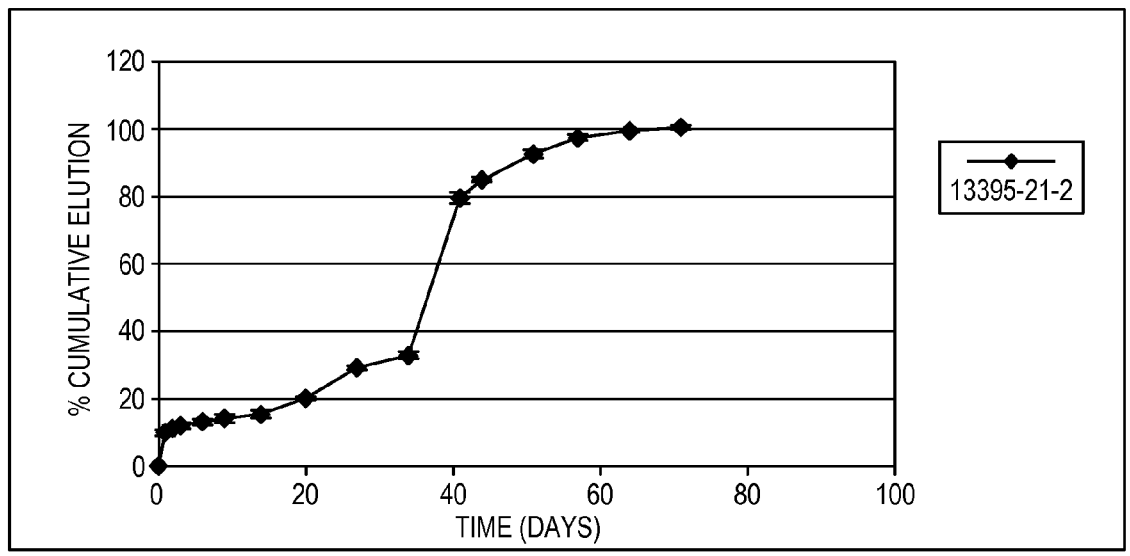
FIG. 27 is a graphic representation of the cumulative elution percentage of clonidine for one formulation.

FIG. 27 is a graphic representation of the cumulative release percentage of clonidine for one formulation produced as indicated in Table 1. The formulation containing 5 wt. % clonidine drug load and the polymer 8515 PLGA had about 100 cumulative release % of drug released from the depot as long as over 75 days, which is suitable for many chronic conditions.

Figure 28:
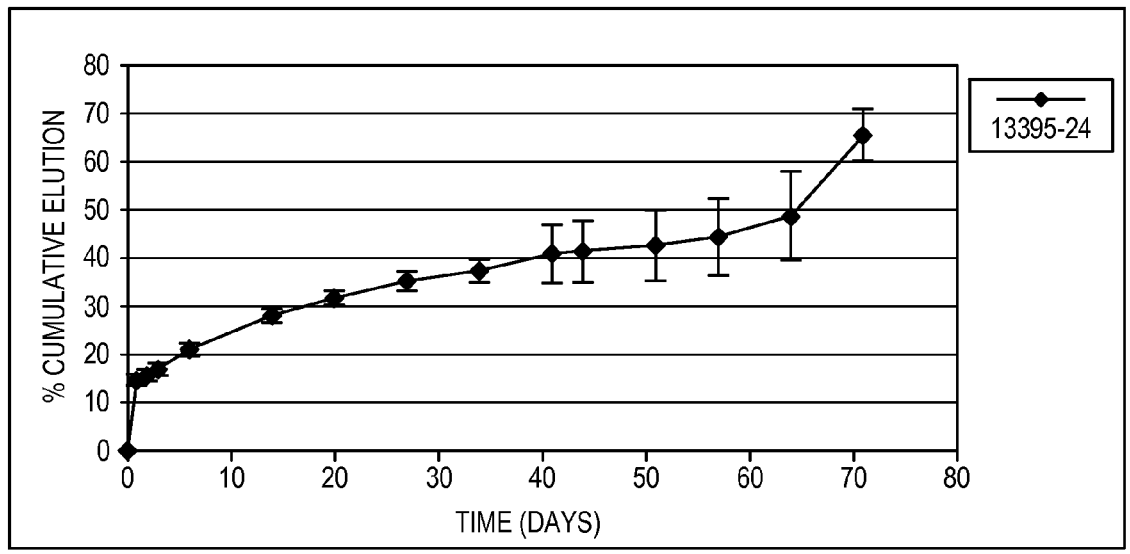
FIG. 28 is a graphic representation of the cumulative release percentage of clonidine for one formulation.

FIG. 28 is a graphic representation of the cumulative release percentage of clonidine for one formulation produced as indicated in Table 1. The formulation containing 5 wt. % clonidine drug load and the polymer 8515 PLGA and Span 65 as a plasticizer had about 65 cumulative release % of drug released from the depot as long as 70 days, which is suitable for many chronic conditions.

Figure 29:
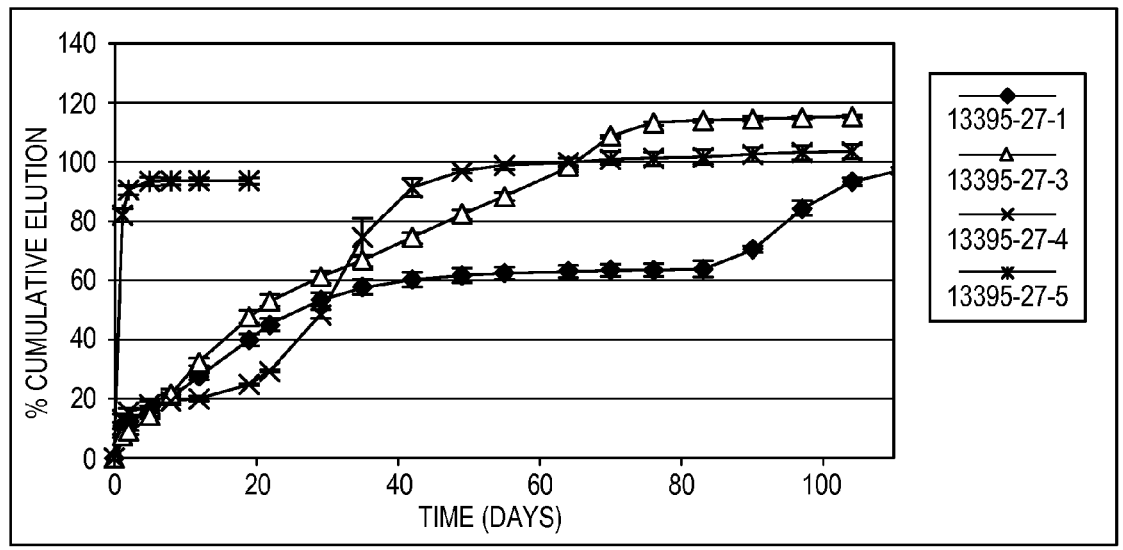
FIG. 29 is a graphic representation of the cumulative elution percentage of clonidine for certain formulations.

FIG. 29 is a graphic representation of the cumulative elution percentage of clonidine for certain formulations produced as indicated in Table 1. All formulations had about 90 to 110 cumulative release % of drug released from the depot for over 100 days, except one, which had about 90 cumulative release % of drug released from the depot for about 20 days.

Figure 30:
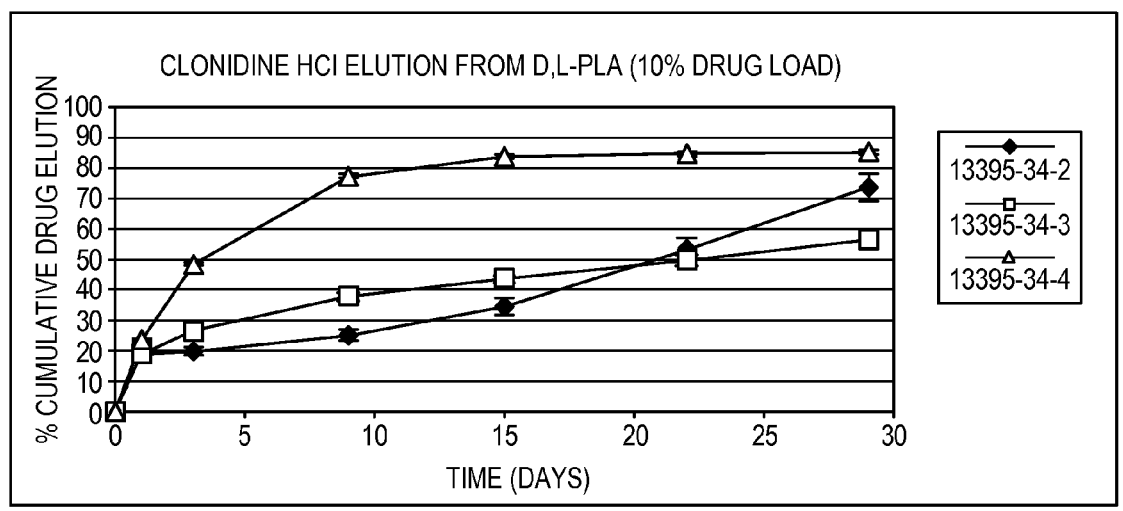
FIG. 30 is a graphic representation of the cumulative elution percentage of clonidine for certain formulations.

FIG. 30 is a graphic representation of the cumulative elution percentage of clonidine for certain formulations produced as indicated in Table 1. All formulations had about 55 to 85 cumulative release % of drug released from the depot for over 28 days.

Figure 31:
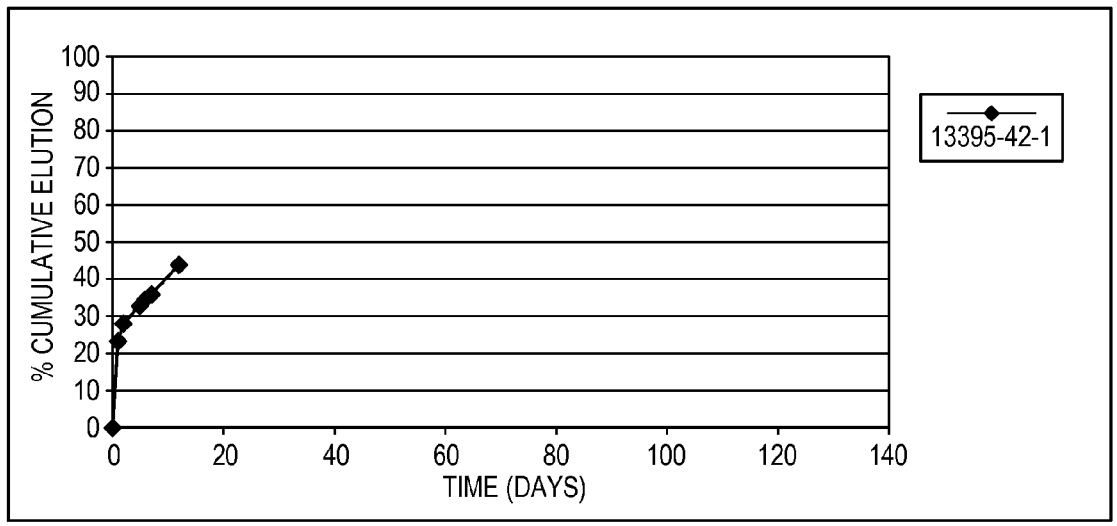
FIG. 31 is a graphic representation of the cumulative elution percentage of clonidine for one formulation.

FIG. 31 is a graphic representation of the cumulative release percentage of clonidine for one formulation produced as indicated in Table 1. The formulation containing 10 wt. % clonidine drug load and the polymer DL-PLA had about 45 cumulative release % of drug released from the depot for about 18 days, which may be suitable for acute conditions.

Figure 32:
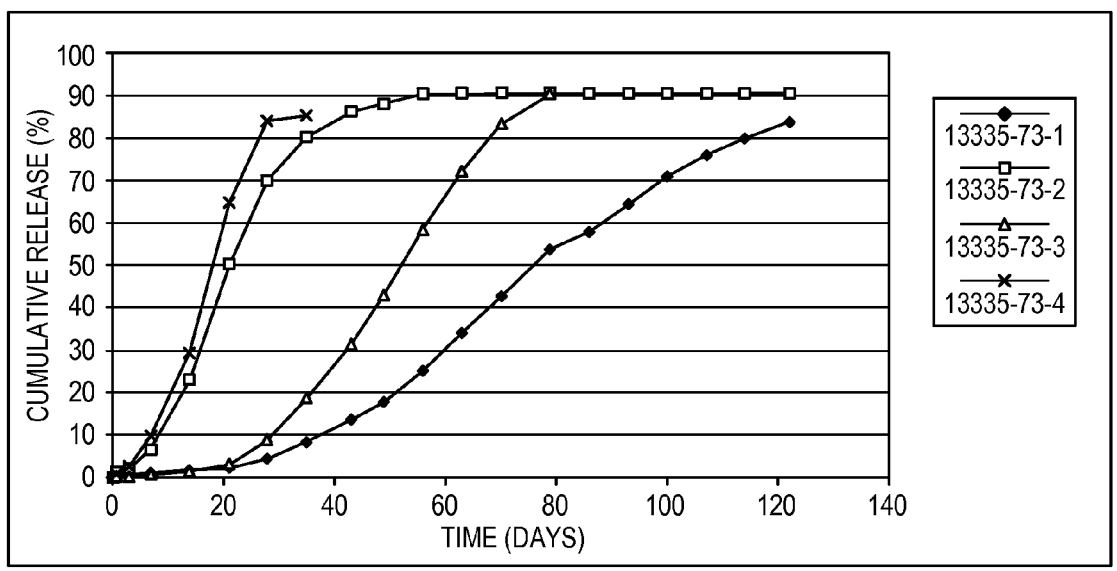
FIG. 32 is a graphic representation of the cumulative release percentage of clonidine for certain formulations.

FIG. 32 is a graphic representation of the cumulative elution percentage of clonidine for certain formulations produced as indicated in Table 2. All formulations had POE and 10% or 20% clonidine drug load. All formulations had about 80 to 90 cumulative release % of drug released from the depot for over 120 days, except one formulation, which released drug within about 35 days.

Figure 33:
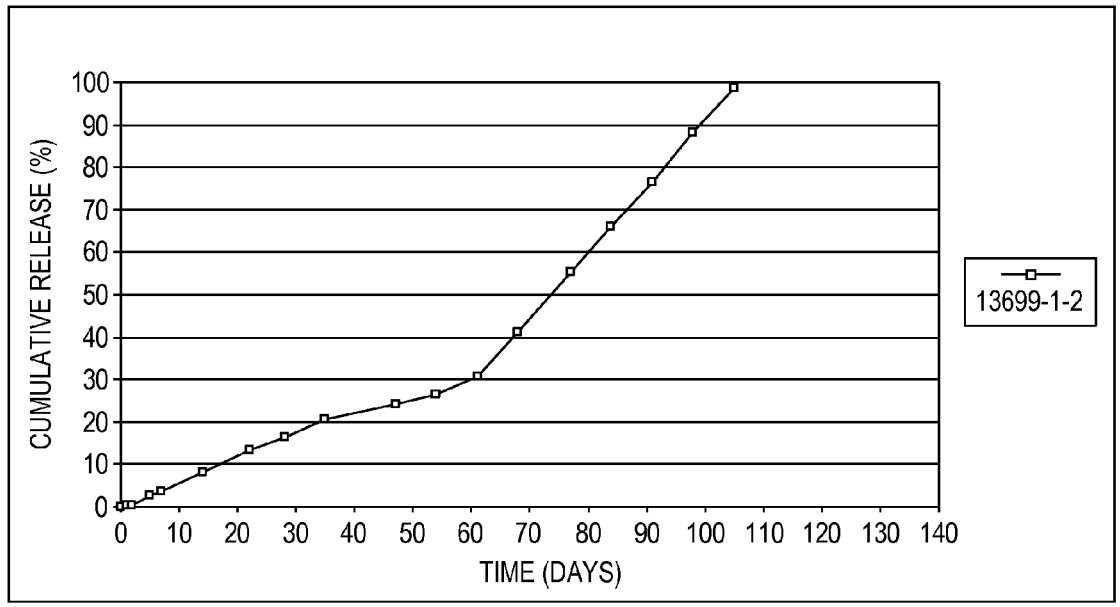
FIG. 33 is a graphic representation of the cumulative release percentage of clonidine for one formulation.

FIG. 33 is a graphic representation of the cumulative release percentage of clonidine for one formulation produced as indicated in Table 2. The formulation containing 10 wt. % clonidine drug load and the polymer POE had about 100% cumulative release % of drug released from the depot for about 100 days, which may be suitable for chronic conditions.

Figure 34:
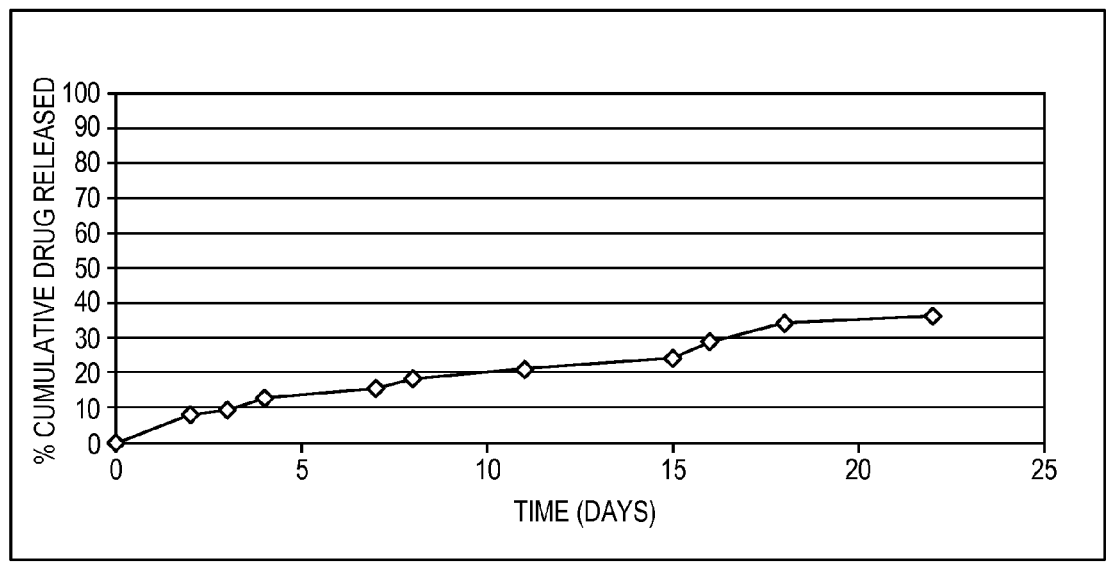
FIG. 34 is a graphic representation of the cumulative release percentage of clonidine for one formulation.

FIG. 34 is a graphic representation of the cumulative release percentage of clonidine for one formulation produced as indicated in Table 2. The formulation had about 35% cumulative release % of clonidine released from the depot for about 23 days.

Example 2

The inventors evaluated the efficacy of a five month Clonidine/Polymer Drug Depot in the Rat Chronic Constriction Injury Model. The animal model was the Bennett Model (Wistar rat). The purpose: To determine whether a five month polymer clonidine-eluting depot can improve pain associated behavioral responses in a rat model of neuropathic pain.

Experimental Design: Four loose chromic gut ligatures, 1 mm apart, were tied around the common sciatic nerve at mid-thigh. Each animal received treatment of a test or control article according to the dosing described in Table 5.

TABLE 5

| Group Number | Treatment | Dose | Comments |
|---|---|---|---|
| 1 | Clonidine | 0.02 mg/kg SC | Clonidine control |
| 2 | 100 DL 7E | 0% | 4 pellets (3 mm × 0.7 mm) |
| 3 | 100 DL 7E | 5% | Clonidine HCl; 4 pellets (3 mm × 0.7 mm) |
| 4 | 100 DL 5E | 5% | 3 pellets (3 mm × 0.7 mm) |
| 5 | 100 DL 5E | 7% | 3 pellets (3 mm × 0.7 mm) |
| 6 | 100 DL 7E | 7% | 3 pellets (3 mm × 0.7 mm) |
| 7 | POE | 0% | 5 pellets (1.5 mm × 0.7 mm) |
| 8 | POE | 10 and 20% | clonidine-base; 5 pellets (1 20% @ 0.7 mm$^{2:}$ 4 10% @ 1.5 mm × 0.7 mm) |

The inventors have conducted the present study for a period of 64 days and have employed the following two tests: (1) the Hargreaves test; and (2) the von Frey test. The Hargreaves Tests of Thermal Hyperalgesia were conducted on days 7, 14, 21, 28, 35, 42, 49, 56 and 63. The von Frey monofilament test of mechanical allodynia (performed the day following Thermal testing) was conducted on days 8, 15, 22, 29, 36, 43, 50, 57 and 64. The results of these tests are summarized in FIGS. 3 and 4 which show the efficacy of clonidine at the recited time periods.

The pain behavioral response (measured as a percentage of baseline) for thermal hyperalgesia (FIG. 3) indicates that clonidine delivered subcutaneously at 0.02 mg/kg/day consistently reduced the behavioral response when compared to either unloaded polymer depots (100 DL 7W Control or POE Control) (58% vs. 45%). All five clonidine-loaded polymer depots were able to reduce pain behavioral responses when compared to unloaded depot; although, each formulation experienced a drop in efficacy at some point after the initial burst of drug at implantation. The pain behavioral response (measured as a percentage of baseline) for mechanical allodynia indicates that clonidine delivered subcutaneously at 0.02 mg/kg/day reduced the behavioral response when compared to either unloaded polymer depots (100 DL 7W Control or POE Control).

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot for reducing, preventing or treating dystonia and/or post-stroke spasticity in a patient in need of such treatment, the drug depot comprising at least one biodegradeable polymer and clonidine or a pharmaceutically acceptable salt thereof in an amount from about 0.1 wt. % to about 30 wt. % of the drug depot, wherein the drug depot has a surface that has an initial burst release of about 5 wt. % to about 35 wt. % of the clonidine or pharmaceutically acceptable salt thereof over a first period of between about 24 and 48 hours and is capable of releasing clonidine over a period of 5 to 135 days, the at least one biodegradable polymer comprising poly(D,L-lactide-co-caprolactone), poly(L-lactide-co-caprolactone), poly(D,L-lactide), or a combination thereof, the drug depot having an inherent viscosity of about 0.5 dL/g to about 0.7 dL/g, about 0.6 dL/g to about 0.8 dL/g, about 0.7 dL/g to about 0.9 dL/g, or about 0.8 dL/g to about 1.0 dL/g and the drug depot has a modulus of elasticity of about $1 \times 10^4$ to about $6 \times 10^5$ dynes/cm$^2$.

2. An implantable drug depot according to claim 1, wherein said clonidine comprises from about 5 wt. % to about 15 wt. % of the drug depot.

3. An implantable drug depot according to claim 1, wherein said clonidine is released in an amount between 0.005 and 1.0 mg per day for a period of 5 to 135 days.

4. An implantable drug depot according to claim 1, wherein said polymer is capable of degrading in 200 days or less after said drug depot is administered to reduce, prevent or treat dystonia and/or post-stroke spasticity.

5. An implantable drug depot according to claim 1, wherein the at least one biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone or a combination thereof.

6. An implantable drug depot according to claim 1, wherein said clonidine is in the form of clonidine hydrochloride or a mixture of clonidine base and a hydrochloride salt.

7. An implantable drug depot according to claim 1, wherein the drug depot releases an effective amount of the clonidine over a period of at least fifty days.

8. A method for treating dystonia and/or post-stroke spasticity, wherein said method comprises implanting the drug depot of claim 1 in an organism to reduce, prevent, or treat dystonia and/or post-stroke spasticity.

9. A method according to claim 8, wherein said clonidine comprises from about 5 wt. % to about 15 wt. % of the drug depot.

10. A method according to claim 8, wherein said biodegradable polymer comprises at least 70 wt. % of the drug depot.

11. A method according to claim 8, wherein said clonidine is capable of being released in an amount between 0.005 and 1.0 mg per day for a period of 5 to 135 days.

12. A method according to claim 8, wherein the drug depot is capable of releasing about 5% to about 100% of said clonidine relative to a total amount of said clonidine loaded in the drug depot over a period of 3 to 200 days after the drug depot is implanted in said organism.

13. A method according to claim 8, wherein said clonidine is in the form of clonidine hydrochloride or a mixture of clonidine and a hydrochloride salt.

14. An implantable drug depot useful for reducing, preventing or treating dystonia and/or post-stroke spasticity in a patient in need of such treatment, the drug depot comprising at least one biodegradeable polymer and a therapeutically effective amount of clonidine, the drug depot being administered at a site to reduce, prevent or treat dystonia and/or post-stroke spasticity, wherein the drug depot has a surface that has an initial burst release of about 5 wt. % to about 35 wt. % of the clonidine or pharmaceutically acceptable salt thereof over a first period of between about 24 and 48 hours and is capable of releasing clonidine at an amount between 0.005 and 1.0 mg per day for a period of 5 to 135 days at the site, the at least one biodegradable polymer comprising poly(D,L-lactide-co-caprolactone), poly(L-lactide-co-caprolactone), poly(D,L-lactide), or a combination thereof, the drug depot having an inherent viscosity of about 0.5 dL/g to about 0.7 dL/g, about 0.6 dL/g to about 0.8 dL/g, about 0.7 dL/g to about 0.9 dL/g, or about 0.8 dL/g to about 1.0 dL/g and the drug depot has a modulus of elasticity of about $1 \times 10^4$ to about $6 \times 10^5$ dynes/cm$^2$.

15. An implantable drug depot according to claim 14, wherein said polymer is capable of degrading in 200 days or less after the drug depot is administered at the site.

16. An implantable drug depot according to claim 14, wherein said clonidine is released in an amount between 0.01 and 0.1 mg per day for a period of 5 to 135 days at the site.

17. An implantable drug depot according to claim 14, wherein said clonidine is present in an amount of about 0.1 to about 30 wt. % of the drug depot and said polymer is present in an amount of about 70 to about 99.9 wt. % of the drug depot.

18. A sustain release composition comprising an effective amount of clonidine or a pharmaceutically acceptable salt thereof in an implantable drug depot, wherein said clonidine or a pharmaceutically acceptable salt thereof has a surface that has an initial burst release of about 5 wt. % to about 35 wt. % over a first period of between about 24 and 48 hours and is present in an amount to relieve post-stroke spasticity and/or dystonia for a period of 5 to 135 days and wherein said implantable drug depot facilitates sustain release of clonidine over said period, the at least one biodegradable polymer comprising poly(D,L-lactide-co-caprolactone), poly(L-lactide-co-caprolactone), poly(D,L-lactide), or a combination thereof, the drug depot having an inherent viscosity of about 0.5 dL/Ug to about 0.7 dL/g, about 0.6 dL/g to about 0.8 dL/g, about 0.7 dL/g to about 0.9 dL/g, or about 0.8 dL/g to about 1.0 dL/g and the drug depot has a modulus of elasticity of about $1 \times 10^4$ to about $6 \times 10^5$ dynes/cm$^2$.

19. A method of making an implantable drug depot of claim 1, the method comprising combining a biocompatible polymer and a therapeutically effective amount of clonidine or a pharmaceutically acceptable salt thereof and forming the implantable drug depot from the combination.

* * * * *